United States Patent
Burnett et al.

(10) Patent No.: US 11,104,902 B2
(45) Date of Patent: Aug. 31, 2021

(54) SPLICE INHIBITING OLIGONUCLEOTIDES

(71) Applicant: CITY OF HOPE, Duarte, CA (US)

(72) Inventors: John C. Burnett, Chatsworth, CA (US); Elizabeth Epps, Mission Viejo, CA (US); John J. Rossi, Azusa, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 16/648,822

(22) PCT Filed: Sep. 21, 2018

(86) PCT No.: PCT/US2018/052293
§ 371 (c)(1),
(2) Date: Mar. 19, 2020

(87) PCT Pub. No.: WO2019/060779
PCT Pub. Date: Mar. 28, 2019

(65) Prior Publication Data
US 2020/0216850 A1    Jul. 9, 2020

Related U.S. Application Data

(60) Provisional application No. 62/562,305, filed on Sep. 22, 2017.

(51) Int. Cl.
*C12N 15/113* (2010.01)
*C12N 15/86* (2006.01)

(52) U.S. Cl.
CPC .......... *C12N 15/1132* (2013.01); *C12N 15/86* (2013.01); *C12N 2310/11* (2013.01); *C12N 2310/33* (2013.01); *C12N 2330/51* (2013.01); *C12N 2740/16043* (2013.01); *C12N 2740/16052* (2013.01)

(58) Field of Classification Search
CPC .......................... C12N 15/1132; C12N 15/86; C12N 2310/11; C12N 2310/33; C12N 2310/51
See application file for complete search history.

(56) References Cited

U.S. PATENT DOCUMENTS

| | | | |
|---|---|---|---|
| 2005/0227917 A1* | 10/2005 | Williams | C12Q 1/6886 435/6.16 |
| 2005/0251872 A1 | 11/2005 | Bear et al. | |
| 2007/0259350 A1* | 11/2007 | Bentwich | C12Q 1/6886 435/6.14 |
| 2009/0092980 A1* | 4/2009 | Arenz | C12Q 1/6811 435/6.12 |
| 2013/0129668 A1 | 5/2013 | Firestein et al. | |
| 2013/0210897 A1* | 8/2013 | Kay | C12N 15/85 514/44 R |
| 2014/0142160 A1* | 5/2014 | Lee | C12N 15/1135 514/44 A |
| 2015/0344892 A1 | 12/2015 | Moeller et al. | |
| 2016/0289681 A1* | 10/2016 | Rossi | C12N 15/86 |
| 2017/0002350 A1* | 1/2017 | Seow | C12N 15/113 |

FOREIGN PATENT DOCUMENTS

| | | | | |
|---|---|---|---|---|
| WO | WO-2015042308 A2 * | 3/2015 | | A61K 48/005 |
| WO | WO-2015/084254 A1 | 6/2015 | | |
| WO | WO-2016138287 A1 * | 9/2016 | | A61P 25/28 |
| WO | WO-2017/018937 A1 | 2/2017 | | |
| WO | WO-2017/123688 A1 | 7/2017 | | |

OTHER PUBLICATIONS

Chung et al. Human Gene Therapy 23:1200-1208 (Year: 2012).*
Aagaard et al. Gene Therapy 15:1536-1549 (Year: 2008).*
Li et al. Methods Enzymol 392:218-26 (Year: 2005).*
Schamberger et al. RNA Biology 9: 1177-1185 (Year: 2012).*
Agranat-Tamiretal. Nucleic Acid Research 42, 4640-4651 (Year: 2014).*
International Search Report dated Feb. 1, 2019, for PCT Application No. PCT/US2018/052293, filed Sep. 21, 2018, 5 pages.
Written Opinion dated Feb. 1, 2019, for PCT Application No. PCT/US2018/052293, filed Sep. 21, 2018, 6 pages.

* cited by examiner

*Primary Examiner* — Brian Whiteman
(74) *Attorney, Agent, or Firm* — Mintz, Levin, Cohn, Ferris, Glovsky and Popeo, P.C.

(57) ABSTRACT

MicroRNAs embedded within an intron, which are called 'mirtrons,' can be used as a platform for expressing one or more shRNA or miRNA mimics in a lentiviral vector. The inventors developed a strategy to improve lentiviral titering by reducing the production of shRNA/miRNA from the vector during packaging through the introduction of splice-inhibiting antisense oligonucleotides during vector packaging, which inhibit the splicing of the mirtron and subsequent processing of the shRNAs/miRNAs. In an aspect is provided a kit comprising an oligonucleotide comprising a mirtron splice site binding sequence and a lentiviral packaging system. In an aspect is provided a method for producing a lentivirus. The method comprises the step of transfecting a cell with an oligonucleotide comprising a mirtron splice site binding sequence and a lentiviral packaging system; thereby producing the lentivirus.

18 Claims, 6 Drawing Sheets

Specification includes a Sequence Listing.

*Viral Production Schematic*  *Viral Transduction Schematic*

No Vector    Vector Alone    2'OMe A    2'OMe C

FIG. 7

5'-UCUUUCCCCCUACCUUCCCCUUAGGCACGUCUGAGAAUGGUGGAUGUGG-3'

(SEQ ID NO:1)

FIG. 8

5'-UAUCCUGCGCCUUUCCACUGCUCUGGUAAGUGCCCAAAUUGCUGGAGGGC-3'

(SEQ ID NO:2)

SPLICE INHIBITING OLIGONUCLEOTIDES

CROSS-REFERENCE TO RELATED APPLICATIONS

This application is a Section 371 U.S. national phase of International Application No. PCT/US2018/052293 filed Sep. 21, 2018, which claims priority to U.S. Application No. 62/562,305 filed Sep. 22, 2017, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant number AI042552, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-681N01US_Sequence_Listing.TXT, created on Aug. 20, 2020, 10,222 bytes, machine format IBM-PC, MS-Windows operating system, is hereby incorporated by reference.

BACKGROUND

Lentiviral constructs containing shRNAs inside of miRNA intronic cassettes may be used as a therapeutic platform for the treatment of numerous diseases. Unfortunately, these vectors have varying levels of self-repression during lentiviral packaging due to vector targeting by processed shRNAs, and, as a result, viral titer remains low in large-scale productions. Provided herein are methods and kits that cure this and other needs in the art.

BRIEF SUMMARY OF THE INVENTION

It has been observed, inter alia, that lentiviral vectors that express short-hairpin RNA (shRNA), microRNA (miRNA), or miRNA mimics can have low packaging titers, since the antisense strand of the shRNA/miRNA can target the complementary sequence on the lentiviral genomic RNA. MicroRNAs embedded within an intron, which are called 'mirtrons,' can also be used as a platform for expressing one or more shRNA or miRNA mimics in a lentiviral vector. These shRNA/miRNA moieties can contribute to poor lentiviral packaging through self-recognition and may also lead to the packaging of alternatively spliced transcripts, which lack the complete mirtron cassette. Moreover, because lentiviral vectors are derived from HIV-1, anti-HIV genes within the lentiviral vector can further inhibit vector packaging, which may severely limit vector titers. For all of these reasons, the inventors developed a strategy to improve lentiviral titering by reducing the production of shRNA/miRNA from the vector during packaging. This is achieved through the introduction of splice-inhibiting antisense oligonucleotides during vector packaging, which inhibit the splicing of the mirtron and subsequent processing of the shRNAs/miRNAs.

Provided herein, for example, are designed novel synthetic splice-inhibiting oligonucleotides (SIO) that will target the splice donor or acceptor regions within the MCM7 gene cassette. In embodiments, blocking splicing during packaging, this approach will prevent the Drosha-mediated processing of all three anti-HIV shRNAs within the intron, as well as the formation of the fully-spliced MCM7 exon. In embodiments, this approach also prevents the possibility of packaging the spliced-form vector transcripts. In embodiments, using conventional designs for SIOs that bind to the splice donor or acceptor junction, the inventors have optimized the dosage requirements, kinetics, and potential off-target effects to the endogenous MCM7 microRNAs (miR-106b, miR-93, and miR-25). In embodiments, the SIO was designed to prevent splicing, but should not induce RNaseH-mediated degradation. In embodiments, oligo chemistries were utilized that are resistant to RNaseH activity, such as 2'-O-Methyl, morpholino, and locked nucleic acid (LNA) substitutions. In embodiments, levels of lentiviral titer can be increased through the addition of synthetic SIOs that inhibit the production of mirtron-derived shRNA/miRNAs during lentiviral packaging, without requiring any modification to the lentiviral packaging system or transfer vector.

In an aspect is provided a kit comprising an oligonucleotide comprising a mirtron splice site binding sequence and a lentiviral packaging system.

In an aspect is provided a method for producing a lentivirus. The method comprises the step of transfecting a cell with an oligonucleotide comprising a mirtron splice site binding sequence and a lentiviral packaging system; thereby producing the lentivirus.

In an aspect is provided oligonucleotides, optionally containing one or more modified nucleotides. Such modifications include, for example, 2'-O-methyl, morpholino, and locked nucleic acid substitutions.

These and other aspects are described in more detail herein.

BRIEF DESCRIPTION OF THE DRAWINGS

SEQ ID NO:7 was the morpholino oligonucleotide used in the Example and discussed with respect to FIGS. 2A-2C, FIGS. 4A-4C, and FIG. 6.

FIG. 2A shows transduced cell images for GFP-containing vector alone vs 2'OMe. FIG. 2B shows 2'-O-methyl-packaged vector GFP expression 72 h post-TXD using raw, unconcentrated virus. GFP-containing vector alone as control. FIG. 2C shows morpholino-packaged vector GFP expression 72 h post-TXD using raw, unconcentrated virus. GFP-containing vector alone as control.

FIG. 4A shows viral titration curves of 1st small-scale packaging of GFP-containing vector alone vs morpholino or 2'O-methyl-treated vector during packaging. FIG. 4B shows 2nd small-scale packaging of GFP-containing vector alone vs morpholino or 2'O-methyl-treated vector during packaging. FIG. 4C shows Morpholino-treated vector packaging titers in TU/mL. Transduces cells were titered using raw, unconcentrated virus and analyzed 5 days after transduction for GFP expression.

FIG. 5A: The MCM7 scaffold allows co-expression of three small RNAs from the single Pol II U1 promoter. S1, S2M, and S3B represent siRNAs targeting the common tat/rev exon, rev, and tat, respectively. U16U5RZ is a nucleolar-localizing ribozyme targeting a conserved U5 region present in all HIV transcripts. U16TAR is a nucleolar-localizing TAR RNA decoy. U16RBE is a nucleolar-localizing Rev binding element RNA decoy. FIG. 5B: The MCM7 cassette with the U1-specific termination sequence (Ult) was cloned into the pHIV7-EGFP lentiviral vector in the forward orientation with respect to the CMV packaging promoter, denoted as "Forward-Ult", while the cassette in the opposite orientation is denoted as "Reverse-Ult." RRE, Rev response element; MCS, multiple cloning site; EGFP, enhanced green fluorescent protein; WPRE, woodchuck hepatitis virus post-transcription regulation element; ΔU3, deleted U3 region to generate a self-inactivating lentiviral vector after integration in targeted cells.

FIG. 7 shows SEQ ID NO:1 where the underlined portion of the sequence is the MCM7 intron and the non-underlined portion of the sequence is the MCM7 exon.

FIG. 8 shows SEQ ID NO: 2 where the underlined portion of the sequence is the MCM7 intron and the non-underlined portion of the sequence is the MCM7 exon.

DETAILED DESCRIPTION

Definitions

Figure 1:
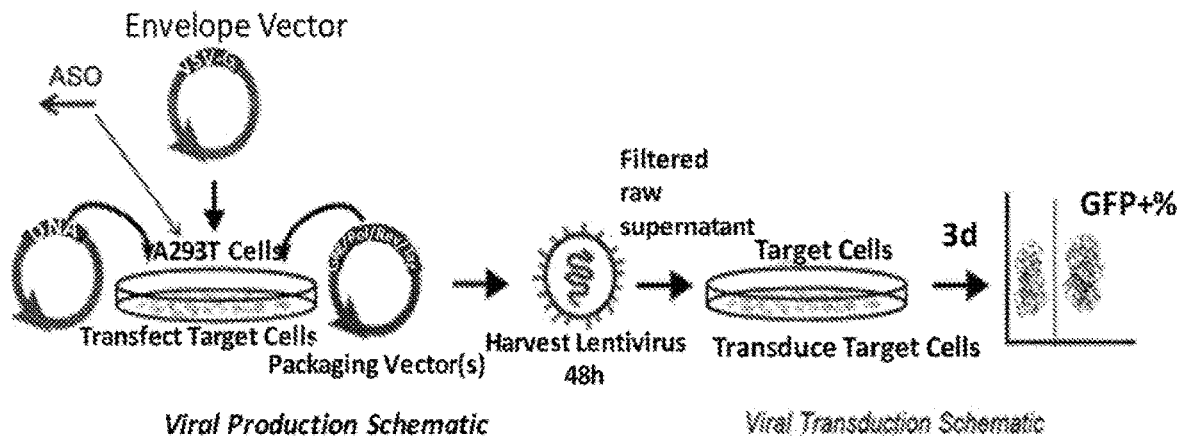
FIG. 1 is a flowchart of Experimental Strategy 1 for preliminary packaging experiments.
Figure 2A:
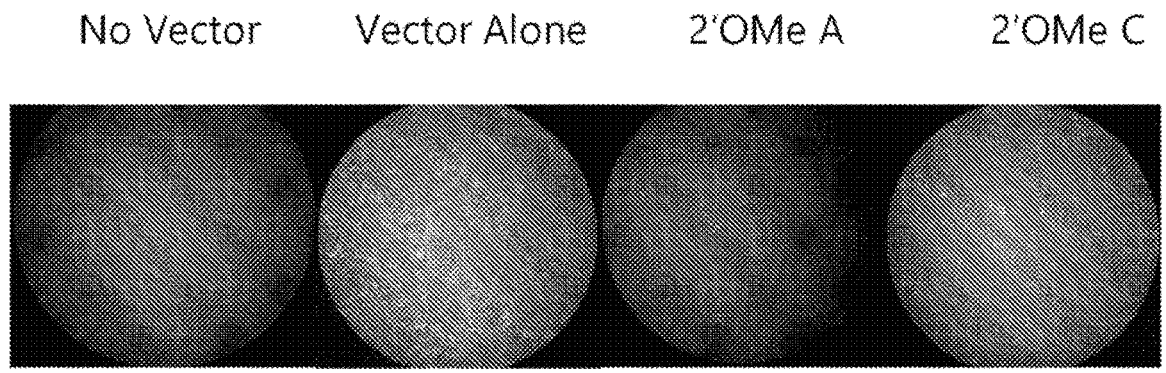
FIGS. 2A-2C.
Figure 2B:
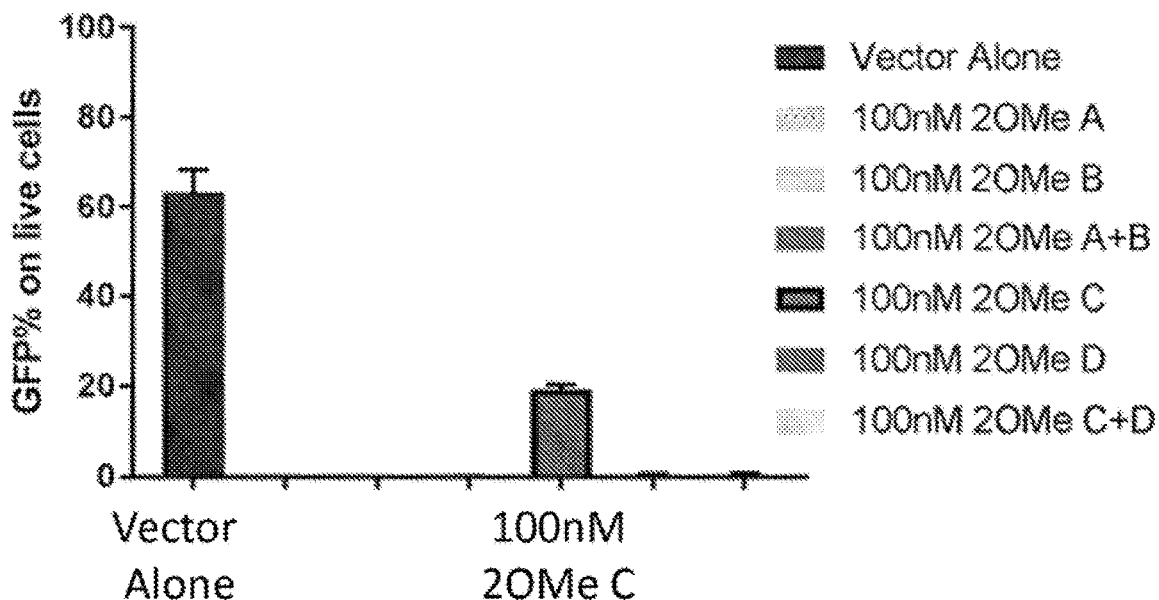
Figure 2C:
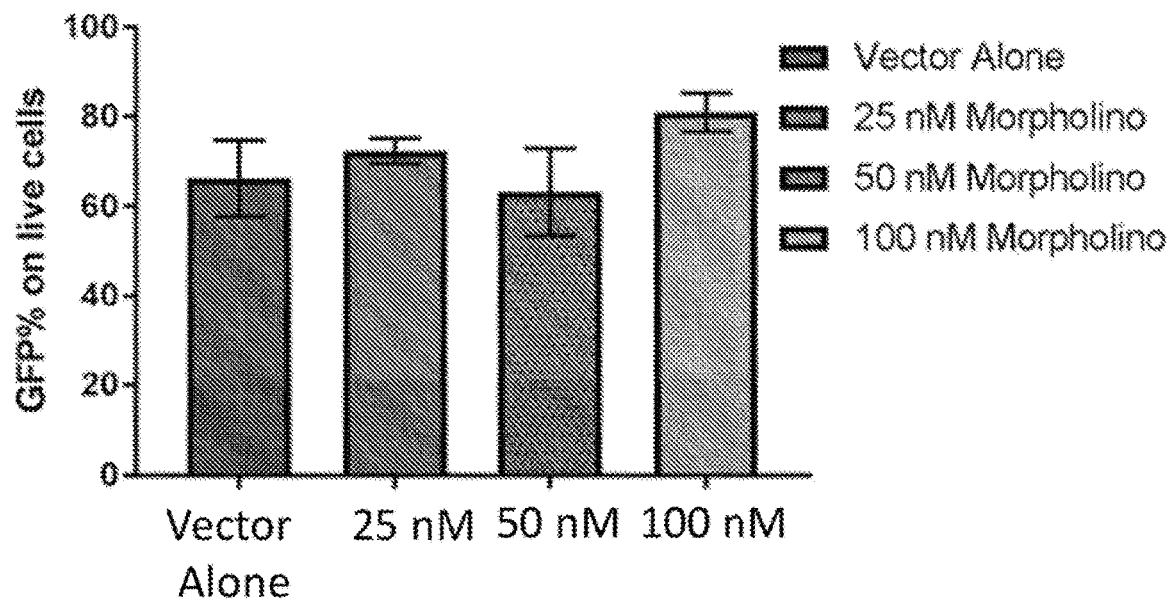
Figure 3:
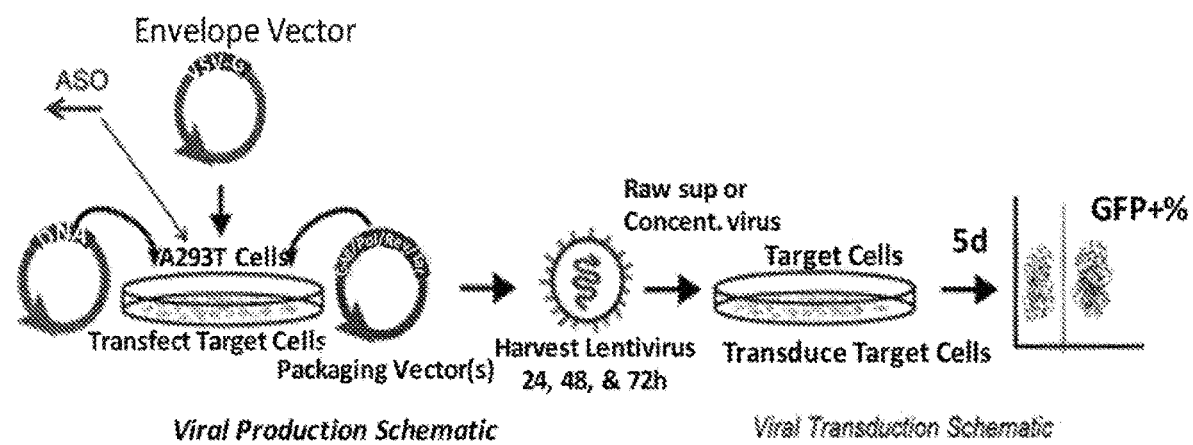
FIG. 3 is a flowchart of Experimental Strategy 2 for small-scale packaging experiments.
Figure 4A:
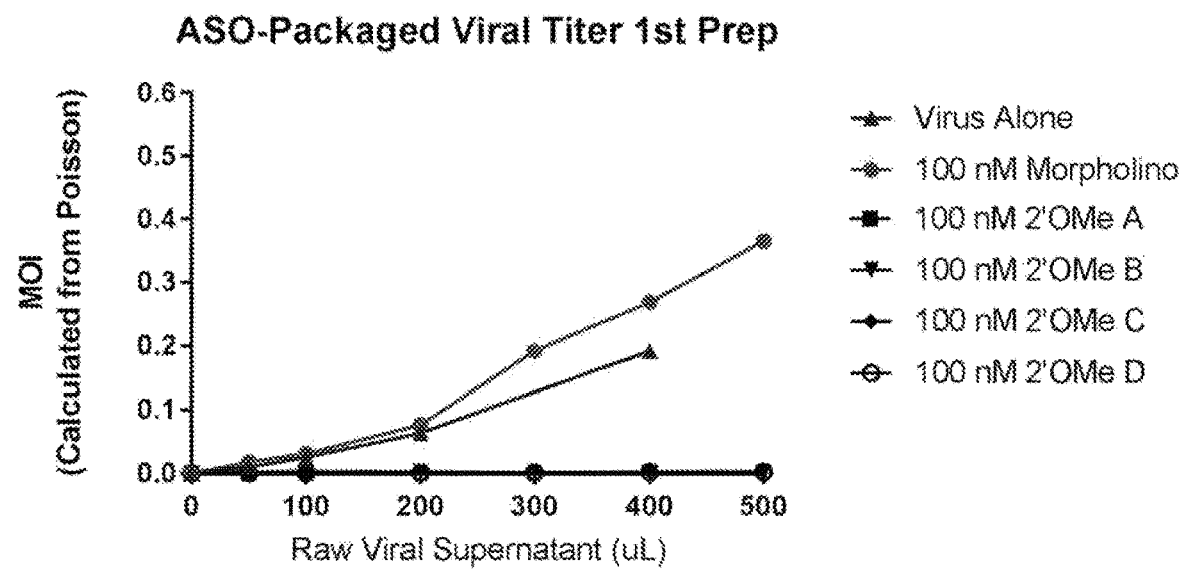
FIGS. 4A-4C.
Figure 4B:
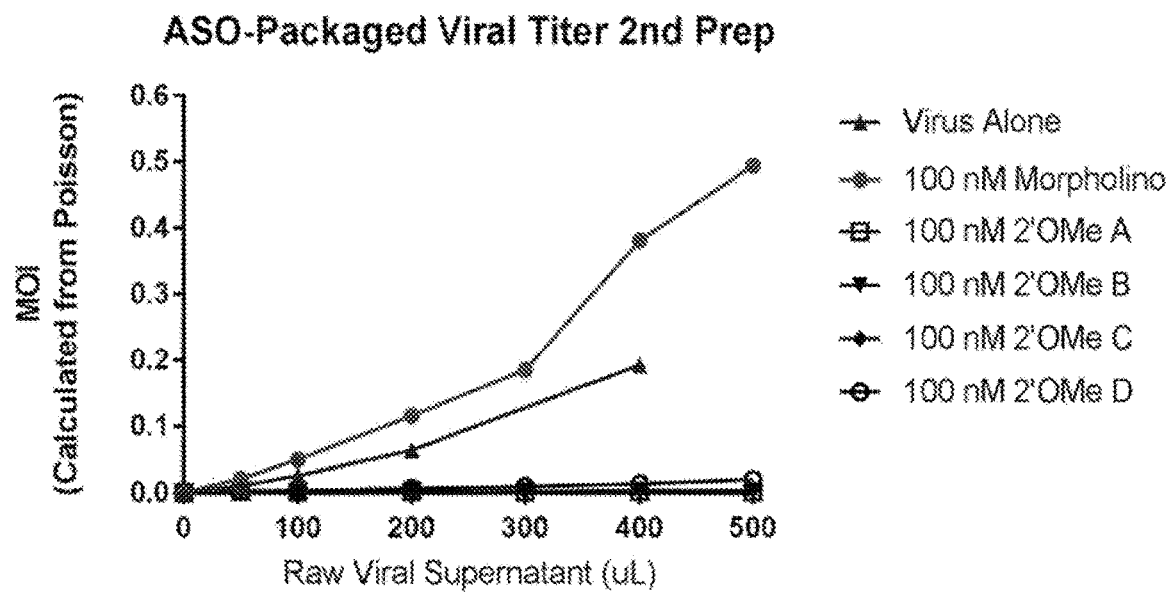
Figure 4C:
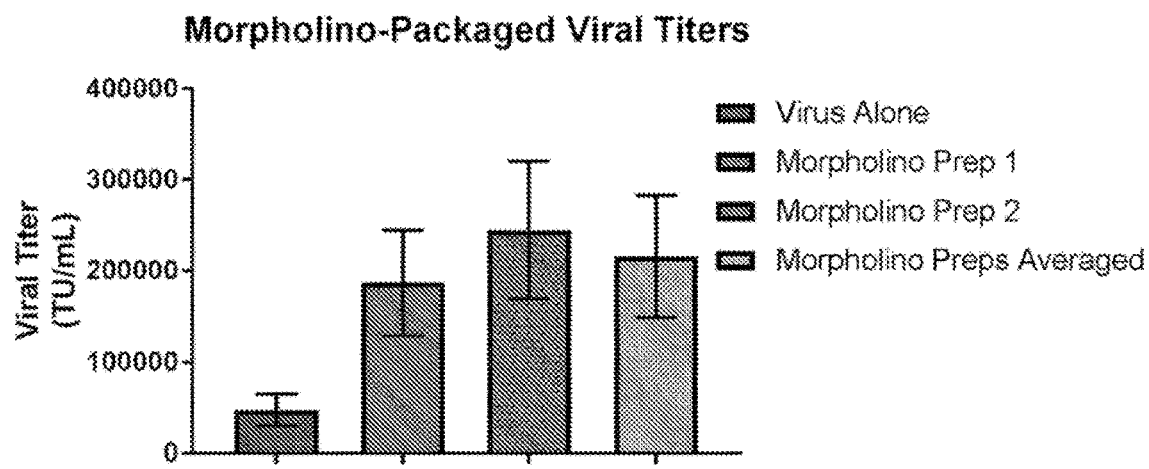

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

As may be used herein, the terms "nucleic acid," "nucleic acid molecule," "nucleic acid oligomer," "oligonucleotide," "nucleic acid sequence," "nucleic acid fragment," and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: (i) Alanine (A), Glycine (G); (ii) Aspartic acid (D), Glutamic acid (E); (iii) Asparagine (N), Glutamine (Q); (iv) Arginine (R), Lysine (K); (v) Isoleucine (I), Leucine (L), Methionine (M), Valine (V); (vi) Phenylalanine (F), Tyrosine (Y), Tryptophan (W); (vii) Serine (S), Threonine (T); and (viii) Cysteine (C), Methionine (M). (see, e.g., Creighton, *Proteins* (1984)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Percentage of sequence identity" or "percent identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "intron" as provided herein is used according to its common meaning in the art and refers to both the nucleic acid sequence within a gene and the corresponding sequence in the unprocessed RNA transcript. "Exon" as provided herein is used according to its common meaning in the art and refers to the nucleic acid sequence within a gene and the corresponding sequence in the unprocessed RNA transcript or processed mature mRNA that encode for a protein. The terms intron and exon likewise apply to RNA sequences which form viral genomes (e.g., RNA viruses, retroviruses (e.g., lentivirus)). With respect to viral genomic RNA, intron refers to non-protein coding viral genomic RNA sequences and exon refers to protein coding viral genomic RNA sequences. In embodiments, the viral genomic RNA sequence is a lentiviral genomic RNA sequence.

The term "mirtron splice site" refers to the bond between a first nucleotide within an intron containing one or more mirtrons and/or one or more one or more microRNA alternative sequences (as defined below) and a second nucleotide within an exon adjacent to said intron. The first nucleotide within the intron may form part of the 3' end of the intron or part of the 5' end of an intron that serve as attachment points for a spliceosome (an RNA-protein complex) which interacts with the intron sequence and catalyzes its excision from the RNA sequence thereby resulting in the biogenesis of one or more mirtrons and/or one or more one or more microRNA alternative sequences. The RNA sequence containing the mirtron splice site may be referred to herein as the mirtron splice site sequence. The mirtron splice site that forms part of the 3' end of the intron is referred to as an acceptor splice site. The mirtron splice site sequence that includes the acceptor splice site may contain an AG nucleic acid sequence. The mirtron splice site that forms part of the 5' end of the intron is referred to as a donor splice site. The mirtron splice site sequence that includes the donor splice site may contain a GU nucleic acid sequence.

In embodiments, the acceptor splice site comprises SEQ ID NO:1 which has the sequence:

5'-UCUUUCCCCCUACCUUCCCCUUAGGCACGUCUGAGAAUGGUGGA UGUGG-3'

With reference to FIG. 7, the underlined portion of the sequence is the MCM7 intron and the non-underlined portion of the sequence is the MCM7 exon. In embodiments, the acceptor splice site is homologous or substantially homologous to SEQ ID NO:1. In embodiments, the acceptor splice site has at least 90% sequence identity to SEQ ID NO:1. In embodiments, the acceptor splice site has at least 95% sequence identity to SEQ ID NO:1. In embodiments, the acceptor splice site is the position between the intron and the exon of SEQ ID NO:1.

In embodiments, the donor splice site comprises SEQ ID NO:2 which has the sequence:

5'-UAUCCUGCGCCUUUCCACUGCUCUGGUAAGUGCCCAAAUUGCUGG AGGGC-3'

With reference to FIG. 8, the underlined portion of the sequence sequence is the MCM7 intron and the non-underlined portion of the sequence sequence is the MCM7 exon. In embodiments, the donor splice site is homologous or substantially homologous to SEQ ID NO:2. In embodiments, the acceptor splice site has at least 90% sequence identity to SEQ ID NO:2. In embodiments, the acceptor splice site has at least 95% sequence identity to SEQ ID NO:2. In embodiments, the donor splice site is the position between the intron and the exon of SEQ ID NO:2.

Figure 5A:
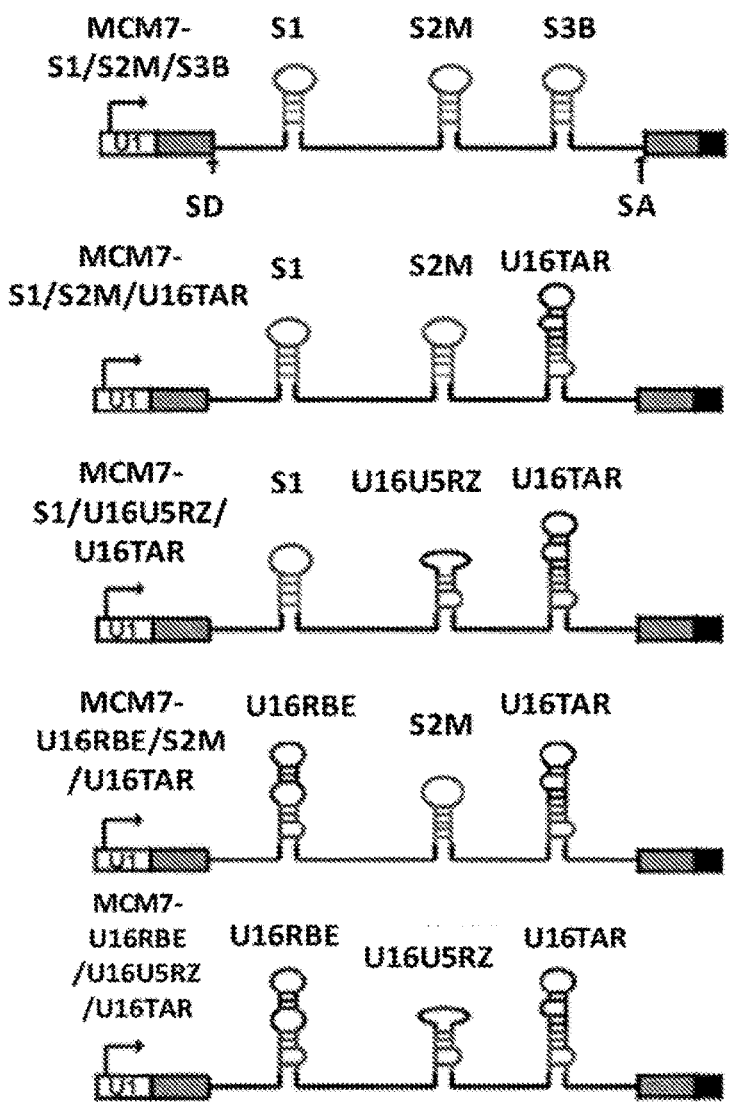
FIGS. 5A-5B provide an overview of MCM7 intron-based lentiviral vectors, as further described in WO 2015/042308, the disclosure of which is incorporated by reference herein in its entirety. The name "MCM7" refers to a naturally occurring polycistronic miRNA cluster located in an intron of the MCM7 gene. Exons and intron of the MCM7 cassette are drawn as grey boxes and black lines, respectively, with splice donors and splice acceptors marked as "SD" and "SA," respectively. Promoters are denoted by white boxes with the arrow indicating directionality, while the terminators are denoted by black boxes. shRNA, U16 snoRNA scaffold, and apical loop anti-HIV RNA insert are shown.
Figure 5B:
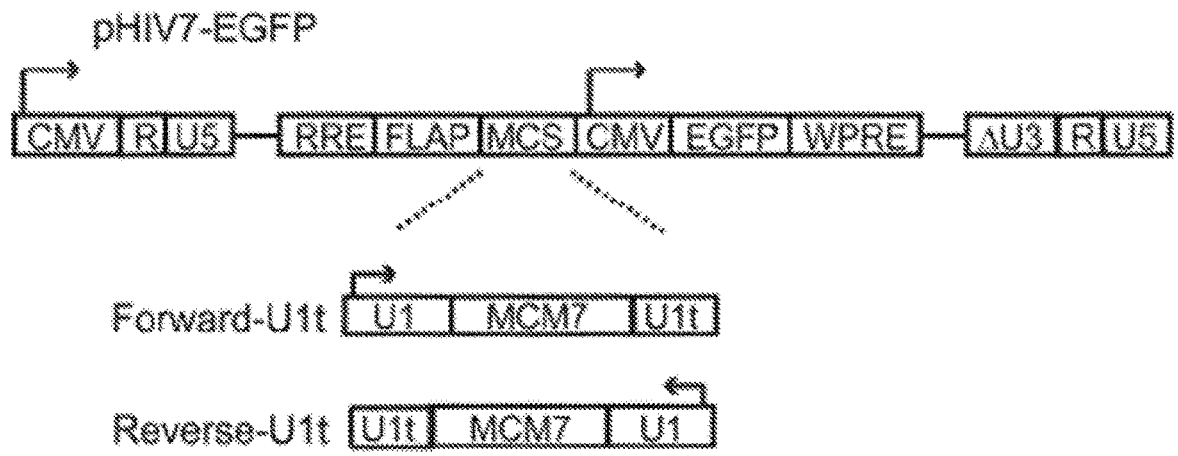
Figure 6:
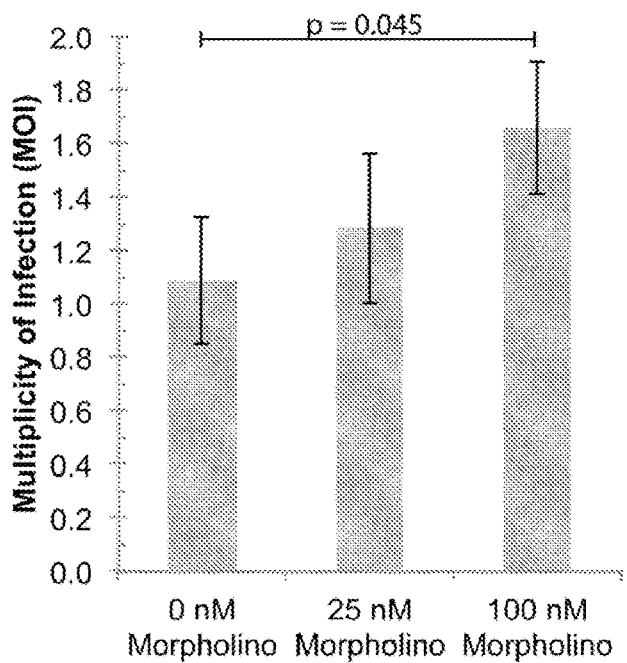
FIG. 6 shows that a morpholino splice inhibiting oligonucleotide (SEQ ID NO:7) improves packaging titer of MCM7-based lentiviral vectors. HEK 293T cells were co-transfected with FGLV-GFP plasmid, helper plasmids, and increasing concentrations of SIO morpholino designed against the MCM7 splice donor site. Vector supernatant was collected and used to transduce naïve reporter cells to evaluate the functional titer of the lentiviral vector by GFP expression.

The term "mirtron" as provided herein refers to a lentiviral intron sequence that, in a natural lentivirus, is an endogenous microRNA sequence located within an intron. In embodiments, the lentivirus used in the compositions and methods provided herein is a non-natural (e.g. recombinant) lentivirus in which one or more endogenous mirtron sequences are removed and/or replaced with one or more microRNA alternative sequences, which is an RNA sequence other than the endogenous microRNA sequences intended to be transfected into the host cell, such as non-endogenous microRNA sequence, RNA aptamer sequence, shRNA sequence (e.g. therapeutic shRNA sequences) or other type of non-endogenous RNA sequence as cargo such as a chimeric antigen receptor for transfection into a T-cell in order to form a CAR T-cell. A single intron may contain one or more mirtron sequences and/or microRNA alternative sequences. Mirtrons and/or microRNA alternative sequences are typically released from the surrounding intron RNA sequence through a splicing event in which the spliceosome attaches to the mirtron splice sites (i.e., an acceptor splice site and/or a donor splice site) and thereby interacts with the intron to excise the mirtron. A mirtron splice site typically function to promote mirtron sequence and/or microRNA alternative sequence excision. A mirtron splice site, for example shown in FIG. 5, includes mirtron splice sites as shown and equivalent splice sites or homologs thereof. In embodiments, the mirtron splice site sequence is 10 to 30 nucleotides in length. In embodiments, the mirtron splice site sequence is 11 to 29 nucleotides in length. In embodiments, the mirtron splice site sequence is 12 to 28 nucleotides in length. In embodiments, the mirtron splice site sequence is 13 to 27 nucleotides in length. In embodiments, the mirtron splice site sequence is 14 to 26 nucleotides in length. In embodiments, the mirtron splice site sequence is 15 to 25 nucleotides in length. In embodiments, the mirtron splice site sequence is 16 to 24 nucleotides in length. In embodiments, the mirtron splice site sequence is 17 to 23 nucleotides in length. In embodiments, the mirtron splice site sequence is 18 to 23 nucleotides in length. In embodiments, the mirtron splice site sequence is 19 to 23 nucleotides in length. In embodiments, the mirtron splice site sequence is 20 to 23 nucleotides in length. In embodiments, the mirtron splice site sequence is 21 to 23 nucleotides in length. In embodiments, the mirtron splice site sequence is 22 to 23 nucleotides in length. In embodiments, the mirtron splice site sequence is 17 to 22 nucleotides in length. In embodiments, the mirtron splice site sequence is 17 to 21 nucleotides in length. In embodiments, the mirtron splice site sequence is 17 to 20 nucleotides in length. In embodiments, the mirtron splice site sequence is 17 to 19 nucleotides in length. In embodiments, the mirtron splice site sequence is 17 to 18 nucleotides in length. In embodiments, the mirtron splice site sequence is 20 nucleotides in length. In embodiments, the mirtron splice site sequence is 19 nucleotides in length. In embodiments, the mirtron splice site sequence is 21 nucleotides in length. The process of excising the mirtron and/or microRNA alternative sequence via splicing to create a free microRNA and/or microRNA alternative sequence capable of undergoing further cellular processing is commonly referred to as "biogenesis." For example, where a microRNA alternative sequence is present (e.g. shRNA), biogenesis may also be used to refer to the excision of a microRNA alternative sequence (e.g. shRNA) from an intron sequence via a splice event. In embodiments, the mirtron splice site as at the junction between the intron containing the microRNA and/or microRNA alternative sequence(s) and the adjacent exon.

A "polycistronic RNA" as provided herein refers to an RNA sequence including more than one (e.g., 2, 3, 4, 5, 6, 7) open reading frame (nucleic acid sequence encoding a polypeptide or an antiviral RNA). A polycistronic RNA may include one promoter controlling the expression of all open reading frames encoded by the polycistronic RNA. In embodiments, the polycistronic RNA includes more than one promoter and one or more of the open reading frames included in the polycistronic RNA are expressed by an independent promoter.

A "siRNA," "small interfering RNA," "small RNA," or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi refers to a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. Non-limiting examples of siRNAs include ribozymes, RNA decoys, short hairpin RNAs (shRNA), microRNAs (miRNA) and small nucleolar RNAs (snoRNA).

"Short hairpin RNA" or "shRNA" refers to RNA with a tight hairpin turn that can be used to silence target gene expression via RNA interference (RNAi).

The term "antisense oligonucleotide" and the like as used herein, refers to a nucleic acid molecule that has a nucleotide sequence complementary to the "sense strand" of a RNA molecule (e.g., lentiviral genomic RNA). The term "sense RNA" as used herein refers to a RNA molecule (e.g., lentiviral genomic RNA) that has a nucleotide sequence complementary to the "antisense strand" of RNA. An antisense oligonucleotide is capable of hybridizing under stringent conditions with a sense strand RNA (e.g., lentiviral genomic RNA). In embodiments, an antisense oligonucleotide may be complementary with all or a portion of a splice site sequence and all or a portion of an exon adjacent to the splice site. In embodiments, an antisense oligonucleotide may be complementary with all or a portion of an acceptor splice site sequence and all or a portion of an exon adjacent to the acceptor splice site. In embodiments, an antisense oligonucleotide may be complementary with all or a portion of a sequence including the donor splice site and all or a portion of an exon adjacent to the donor splice site. In embodiments, the antisense oligonucleotide is a mirtron splice site binding sequence.

The term "antiviral RNA" as provided herein refers to an RNA that is capable of inhibiting the activity (e.g., transcription, translation, replication, infectivity) of a virus. In embodiments, the antiviral RNA binds to a target viral nucleic and reduces transcription of the target viral nucleic acid or reduces the translation of the target viral nucleic acid (e.g. mRNA) or alters transcript splicing. In embodiments, the antiviral RNA is a nucleic acid that is capable of binding (e.g. hybridizing) to a target viral nucleic acid (e.g. an Rev RNA) and reducing translation of the target viral nucleic acid. The target viral nucleic acid is or includes one or more target nucleic acid sequences to which the antiviral RNA binds (e.g. hybridizes). In embodiments, the antiviral RNA is or includes a sequence that is capable of hybridizing to at least a portion of a target viral nucleic acid at a target viral nucleic acid sequence. Non-limiting examples of an antiviral RNA include siRNAs, ribozymes, RNA decoys, snoRNAs and shRNAs.

A "MCM7 gene" as referred to herein includes any of the recombinant or naturally-occurring forms of the gene encoding DNA replication licensing factor MCM7 or variants or homologs thereof that maintain MCM7 protein activity (e.g. within at least 50%, 80%, 90%, 95%, 96%, 97%, 98%, 99% or 100% activity compared to MCM7). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MCM7 polypeptide. In embodiments, the MCM7 gene is substantially identical to the nucleic acid identified by the NCBI reference number Gene ID: 4176 or a variant or homolog having substantial identity thereto.

In embodiments, the MCM7 gene forms part of the lentiviral genomic RNA (and thus, the a lentiviral packaging system). The MCM7 protein encoding gene includes a polycistronic mirtron cluster (i.e., 3 microRNA sequences) located within an intron. The mirtrons within the mirtron cluster may, in embodiments, be replaced with one or more microRNA alternative sequences (e.g. shRNAs or miRNAs) as described above. Useful methods for replacing mirtron sequences are described, for example, in WO 2015/042308. In embodiments, mirtrons present in the MCM7 gene are replaced with one or more microRNA alternative sequences, such as exogenous shRNAs or miRNAs. In embodiments, mirtrons present in the MCM7 gene are replaced with one or more microRNA alternative sequences, such as shRNAs or miRNAs useful for treatment of a disease.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection, and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007)*Nat. Methods* 4:119-20.

"Lentivirus" refers to virus from the family Retroviridae and the genus *Lentivirus*. Exemplary lentivirus include human immunodeficiency virus (HIV-1), simian immunodeficiency virus, bovine immunodeficiency virus, equine infectious anemia virus, feline immunodeficiency virus, and the like. In embodiments, the lentivirus is human immunodeficiency virus (HIV-1). In embodiments, the lentivirus is a pHIV7-EGFP lentivirus. In embodiments, the lentivirus is a non-natural lentivirus, such as recombinant lentivirus.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The term "plasmid" refers to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

A "lentiviral packaging systems" as used herein refers to systems used to produce lentivirus. "Second generation lentiviral packaging system" and "third generation lentiviral packaging system" refer to distinct systems useful for producing lentivirus. These systems are well-known in the art, as described, for example, in Barde et al, "Production and Titration of Lentiviral Vectors," Current Protocols in Neuroscience, Volume 53, Issue 1 (2010) (also cited as Current Protocols in Neuroscience 4.21.1-4.21.23 (October 2010)). The main difference between the second generation and third generation lentiviral packaging systems is the total number of plasmids used to generate a lentiviral particle, i.e., three plasmids are used to generate a lentiviral particle in the second generation system and four plasmids are used to generate a lentiviral particle in the third generation system. Both the second and third generation lentiviral packaging systems require the following components: (i) a lentiviral plasmid vector containing the gene(s) of interest; (ii) a packaging plasmid(s), and (iii) an envelope plasmid. In embodiments, the packaging system includes nucleic acids (e.g. one or more plasmids) encoding lentiviral proteins necessary for production of lentivirus within the host cell. Exemplary packaging proteins are Gag, Pol, Rev, and Tat and envelope proteins.

In the second generation lentiviral packaging system, the lentiviral genome is distributed across three plasmids, including a packaging plasmid, an envelope plasmid, and a transfer plasmid. The packaging plasmid encodes the Gag, Pol, Rev, and Tat genes and a promoter sequence. The envelope plasmid encodes an envelope protein (e.g., VSV-G) and a promoter sequence. The transfer plasmid encodes the transgene (e.g., cDNA, shRNA, miRNA) flanked by long terminal repeat sequences (e.g., 5' LTR, 3' LTR) and, optionally, a promoter sequence upstream of the transgene.

The third generation lentiviral packaging system distributes the lentiviral genome across four plasmids, including two packaging plasmids, an envelope plasmid, and a transfer plasmid. One packaging plasmid encodes the Rev gene and a promoter sequence (e.g., CMV promoter), while the second packaging plasmid encodes the Gag and Pol genes and a promoter sequence (e.g., CMV promoter). The envelope plasmid encodes an envelope protein (e.g., VSV-G) and a promoter sequence (e.g., CMV promoter). The transfer plasmid contains a chimeric 5' LTR fused to a heterologous promoter, a transgene of interest and a 3' LTR.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

"Contacting" is used in accordance with its plain ordinary meaning and refers to the process of allowing at least two distinct species (e.g. sense and antisense RNA) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to an antisense oligonucleotide binding to a splice site (e.g., acceptor splice site, donor splice site) means negatively affecting (e.g. decreasing or preventing) RNA excision (e.g., mirtron biogenesis) compared to RNA excision in the absence of the inhibitor. In embodiments inhibition means negatively affecting (e.g. decreasing) the concentration or levels of free RNA sequence (e.g., miRNA, shRNA) relative to the concentration or level of the free RNA sequence (e.g., miRNA, shRNA) in the absence of the inhibitor.

The terms "inhibitor," "repressor" or "antagonist" or "downregulator" interchangeably refer to a substance (e.g., antisense oligonucleotide) capable of detectably decreasing the excision or activity of a given RNA sequence (e.g., miRNA, shRNA). The antagonist can decrease the probability of excision or activity 10%, 20%, 30%, 40%, 50%, 60%, 70%, 80%, 90% or more in comparison to a control in the absence of the antagonist. In certain instances, the probability of excision or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "virus" or "virus particle" are used according to their plain ordinary meaning within virology and refer to a virion including the viral genome (e.g. DNA, RNA, single strand, double strand), viral capsid and associated proteins, and in the case of enveloped viruses (e.g. herpesvirus), an envelope including lipids and optionally components of host cell membranes, and/or viral proteins.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

Kits

Provided herein are kits useful for increasing lentiviral titers. In embodiments, the kit does not modify existing lentiviral packaging systems. The kit provided herein utilizes an antisense oligonucleotide that hybridizes to a mirtron splice site sequence (e.g., including an acceptor splice site or a donor splice site) within the lentiviral genomic RNA, for example at the mirtron splice sites of an MCMI gene, thereby preventing the attachment of a spliceosome and subsequent excision of a miRNA and/or a shRNA from the intron. By preventing biogenesis of the miRNA and/or shRNA, the miRNA and/or shRNA cannot be processed and subsequently hybridize to the lentiviral genomic RNA to induce lentiviral genomic RNA degradation. In addition, use of an antisense oligonucleotide that prevents splicing will ensure that the full length lentiviral RNA genome will be packaged into the lentiviral particle. Thus, in an aspect is provided a kit comprising: (i) an oligonucleotide comprising a mirtron splice site binding sequence; and (ii) a lentiviral packaging system. In embodiments, the antisense oligonucleotide that hybridizes to a mirtron splice site sequence (e.g. a mirtron splice site binding sequence) binds to at least one nucleotide on either side of the splice site, e.g. 5' to the splice site or 3' to the splice site.

As discussed above, a lentiviral packaging system refers to a system used to produce lentivirus. Lentiviral packaging systems may be second or third generation lentiviral packaging systems. In aspects, the lentiviral packaging system is a second generation lentiviral packaging system. In aspects, the lentiviral packaging system is a third generation lentiviral packaging system.

An "oligonucleotide comprising a mirtron splice site binding sequence" refers to an antisense oligonucleotide capable of hybridizing to a mirtron splice site sequence, thereby preventing miRNA biogenesis through splicing. In embodiments, hybridization of the mirtron splice site binding sequence to the mirtron splice site sequence does not induce RNA degradation through, for example, RNAseH mediated mechanisms. To circumvent degradation of the lentiviral genomic RNA upon hybridization of the mirtron splice site binding sequence, the mirtron splice site binding sequence may include modified oligonucleotides that are resistant to RNAseH degradation. Non-limiting examples of modified oligonucleotides include 2'-O-alkyl, 2'-O-Methyl, 2'-deoxy-2'fluoro, 2'-deoxy, a universal base, 5-C-methyl, an inverted deoxy abasic residue incorporation, a positive backbone; non-ionic backbones, modified sugars, and non-ribose backbones (e.g. phosphorodiamidate morpholino oligonucleotides), and locked nucleic acids (LNAs).

"Morpholino" or "phosphorodiami date morpholino" refer to a nucleic acid in which a methylenemorpholine ring replaces a ribose or deoxyribose sugar moiety and a non-ionic phosphorodiamidate linkage replaces an anionic phosphate moiety.

In embodiments, the oligonucleotide comprising a mirtron splice site binding sequence is SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is a modified oligonucleotide. In embodiments, the oligonucleotide comprising a mirtron splice site binding sequence is a modified oligonucleotide of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the modified oligonucleotide is a 2'-O-methyl modified oligonucleotide. In embodiments, the modified oligonucleotide is a morpholino. In embodiments, the modified oligonucleotide is a LNA. In embodiments, the modified oligonucleotide includes a combination of LNA, 2'-O-methyl, and morpholino modified oligonucleotides. In embodiments, the nucleic acid comprising a mirtron splice site binding sequence comprises at least one modified nucleic acid. In embodiments, the nucleic acid comprising a mirtron splice site binding sequence comprises from 1 to about 20 modified nucleic acids. In embodiments, the nucleic acid comprising a mirtron splice site binding sequence comprises from 1 to about 15 modified nucleic acids. In embodiments, the nucleic acid comprising a mirtron splice site binding sequence comprises from 1 to about 10 modified nucleic acids. In embodiments, the nucleic acid comprising a mirtron splice site binding sequence comprises from 1 to about 5 modified nucleic acids. In embodiments, the nucleic acid comprising a mirtron splice site binding sequence contains 1 modified nucleic acid. In embodiments, the nucleic acid comprising a mirtron splice site binding sequence contains 2 modified nucleic acids. In embodiments, the nucleic acid comprising a mirtron splice site binding sequence contains 3 modified nucleic acids. In embodiments, the nucleic acid comprising a mirtron splice site binding sequence contains 4 modified nucleic acids. In embodiments, the nucleic acid comprising a mirtron splice site binding sequence contains 5 modified nucleic acids. In embodiments, the nucleic acid comprising a mirtron splice site binding sequence contains 6 modified nucleic acids. In embodiments, the nucleic acid comprising a mirtron splice site binding sequence contains 7 modified nucleic acids. In embodiments, the nucleic acid comprising a mirtron splice site binding sequence contains 8 modified nucleic acids. In embodiments, the nucleic acid comprising a mirtron splice site binding sequence contains 9 modified nucleic acids. In embodiments, the nucleic acid comprising a mirtron splice site binding sequence contains 10 modified nucleic acids. In embodiments, the nucleic acid comprising a mirtron splice site binding sequence contains 11 modified nucleic acids. In embodiments, the nucleic acid comprising a mirtron splice site binding sequence contains 12 modified nucleic acids. In embodiments, the nucleic acid comprising a mirtron splice site binding sequence contains 13 modified nucleic acids. In embodiments, the nucleic acid comprising a mirtron splice site binding sequence contains 14 modified nucleic acids. In embodiments, the nucleic acid comprising a mirtron splice site binding sequence contains 15 modified nucleic acids. In embodiments, the nucleic acid comprising a mirtron splice site binding sequence contains 16 modified nucleic acids. In embodiments, the nucleic acid comprising a mirtron splice site binding sequence contains 17 modified nucleic acids. In embodiments, the nucleic acid comprising a mirtron splice site binding sequence contains 18 modified nucleic acids. In embodiments, the nucleic acid comprising a mirtron splice site binding sequence contains 19 modified nucleic acids. In embodiments, the nucleic acid comprising a mirtron splice site binding sequence contains 20 modified nucleic acids. In embodiments, the nucleic acid comprising a mirtron splice site binding sequence contains 21 modified nucleic acids. In embodiments, the nucleic acid comprising a mirtron splice site binding sequence contains 22 modified nucleic acids. In embodiments, the nucleic acid comprising a mirtron splice site binding sequence contains 23 modified nucleic acids. In embodiments, the nucleic acid comprising a mirtron splice site binding sequence contains 24 modified nucleic acids. In embodiments, the nucleic acid comprising a mirtron splice site binding sequence contains 25 modified nucleic acids.

In embodiments, the oligonucleotide comprising a mirtron splice site binding sequence is a nucleic acid that binds to a region of the MCM1 splice donor site and comprises one of the following sequences:

```
                                           (SEQ ID NO: 3)
5'-CCCTCCAGCAATTTGGGCACTTACC-3'

(SEQ ID NO: 4)
5'-CCTCCAGCAATTTGGGCACTTACCA-3'

(SEQ ID NO: 5)
5'-CTCCAGCAATTTGGGCACTTACCAG-3'

(SEQ ID NO: 6)
5'-TCCAGCAATTTGGGCACTTACCAGA-3'

(SEQ ID NO: 7)
5'-CCAGCAATTTGGGCACTTACCAGAG-3'

(SEQ ID NO: 8)
5'-CAGCAATTTGGGCACTTACCAGAGC-3'

(SEQ ID NO: 9)
5'-AGCAATTTGGGCACTTACCAGAGCA-3'

(SEQ ID NO: 10)
5'-GCAATTTGGGCACTTACCAGAGCAG-3'

(SEQ ID NO: 11)
5'-CAATTTGGGCACTTACCAGAGCAGT-3'

(SEQ ID NO: 12)
5'-AATTTGGGCACTTACCAGAGCAGTG-3'

(SEQ ID NO: 13)
5'-ATTTGGGCACTTACCAGAGCAGTGG-3'

(SEQ ID NO: 14)
5'-TTTGGGCACTTACCAGAGCAGTGGA-3'

(SEQ ID NO: 15)
5'-TTGGGCACTTACCAGAGCAGTGGAA-3'

(SEQ ID NO: 16)
5'-TGGGCACTTACCAGAGCAGTGGAAA-3'

(SEQ ID NO: 17)
5'-GGGCACTTACCAGAGCAGTGGAAAG-3'

(SEQ ID NO: 18)
5'-GGCACTTACCAGAGCAGTGGAAAGG-3'

(SEQ ID NO: 19)
5'-GCACTTACCAGAGCAGTGGAAAGGC-3'

(SEQ ID NO: 20)
5'-CACTTACCAGAGCAGTGGAAAGGCG-3'
```

```
                                              (SEQ ID NO: 21)
5'-ACTTACCAGAGCAGTGGAAAGGCGC-3'

(SEQ ID NO: 22)
5'-CTTACCAGAGCAGTGGAAAGGCGCA-3'

(SEQ ID NO: 23)
5'-TTACCAGAGCAGTGGAAAGGCGCAG-3'

(SEQ ID NO: 24)
5'-TACCAGAGCAGTGGAAAGGCGCAGG-3'

(SEQ ID NO: 25)
5'-ACCAGAGCAGTGGAAAGGCGCAGGA-3'

(SEQ ID NO: 26)
5'-CCAGAGCAGTGGAAAGGCGCAGGAT-3'
```

In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is a modified oligonucleotide. Non-limiting examples of modifications that can be to the oligonucleotides of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; and SEQ ID NO:26 include 2'-O-alkyl, 2'-O-methyl, 2'-deoxy-2'fluoro, 2'-deoxy, a universal base, 5-C-methyl, an inverted deoxy abasic residue incorporation, a positive backbone; non-ionic backbones, modified sugars, and non-ribose backbones (e.g. phosphorodiamidate morpholino oligonucleotides), and locked nucleic acids (LNAs). In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is a 2'-O-alkyl modified oligonucleotide. In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is a 2'-O-methyl modified oligonucleotide. In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is a 2'-deoxy-2'fluoro modified oligonucleotide. In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is modified with a non-ribose backbone, such as phosphorodiamidate morpholino. In embodiments, SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26 is a phosphorodiamidate morpholino modified oligonucleotide.

In embodiments, the oligonucleotide comprising a mirtron splice site binding sequence is a nucleic acid that binds to a region of the MCMI splice acceptor site and comprises one of the following amino acid sequences:

```
                                              (SEQ ID NO: 27)
5'-CACATCCACCATTCTCAGACGTGCC-3'

(SEQ ID NO: 28)
5'-ACATCCACCATTCTCAGACGTGCCT-3'

(SEQ ID NO: 29)
5'-CATCCACCATTCTCAGACGTGCCTA-3'

(SEQ ID NO: 30)
5'-ATCCACCATTCTCAGACGTGCCTAA-3'

(SEQ ID NO: 31)
5'-TCCACCATTCTCAGACGTGCCTAAG-3'

(SEQ ID NO: 32)
5'-CCACCATTCTCAGACGTGCCTAAGG-3'

(SEQ ID NO: 33)
5'-CACCATTCTCAGACGTGCCTAAGGG-3'

(SEQ ID NO: 34)
5'-ACCATTCTCAGACGTGCCTAAGGGG-3'

(SEQ ID NO: 35)
5'-CCATTCTCAGACGTGCCTAAGGGGA-3'

(SEQ ID NO: 36)
5'-CATTCTCAGACGTGCCTAAGGGGAA-3'

(SEQ ID NO: 37)
5'-ATTCTCAGACGTGCCTAAGGGGAAG-3'

(SEQ ID NO: 38)
5'-TTCTCAGACGTGCCTAAGGGGAAGG-3'

(SEQ ID NO: 39)
5'-TCTCAGACGTGCCTAAGGGGAAGGT-3'

(SEQ ID NO: 40)
5'-CTCAGACGTGCCTAAGGGGAAGGTA-3'

(SEQ ID NO: 41)
5'-TCAGACGTGCCTAAGGGGAAGGTAG-3'

(SEQ ID NO: 42)
5'-CAGACGTGCCTAAGGGGAAGGTAGG-3'

(SEQ ID NO: 43)
5'-AGACGTGCCTAAGGGGAAGGTAGGG-3'

(SEQ ID NO: 44)
5'-GACGTGCCTAAGGGGAAGGTAGGGG-3'

(SEQ ID NO: 45)
5'-ACGTGCCTAAGGGGAAGGTAGGGGG-3'

(SEQ ID NO: 46)
5'-CGTGCCTAAGGGGAAGGTAGGGGGG-3'
```

```
                                              (SEQ ID NO: 47)
5'-GTGCCTAAGGGGAAGGTAGGGGGGA-3'

(SEQ ID NO: 48)
5'-TGCCTAAGGGGAAGGTAGGGGGGAA-3'

(SEQ ID NO: 49)
5'-GCCTAAGGGGAAGGTAGGGGGGAAA-3'

(SEQ ID NO: 50)
5'-CCTAAGGGGAAGGTAGGGGGGAAAG-3'
```

In embodiments, SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a modified oligonucleotide. Non-limiting examples of modifications that can be to the oligonucleotides of SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 include 2'-O-alkyl, 2'-O-methyl, 2'-deoxy-2'fluoro, 2'-deoxy, a universal base, 5-C-methyl, an inverted deoxy abasic residue incorporation, a positive backbone; non-ionic backbones, modified sugars, and non-ribose backbones (e.g. phosphorodiamidate morpholino oligonucleotides), and locked nucleic acids (LNAs). In embodiments, SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a 2'-O-alkyl modified oligonucleotide. In embodiments, SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a 2'-O-methyl modified oligonucleotide. In embodiments, SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a 2'-deoxy-2'fluoro modified oligonucleotide. In embodiments, SEQ ID NO:27; SEQ ID NO:28; SEQ ID NO:29; SEQ ID NO:30; SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a 2'-deoxy modified oligonucleotide. In embodiments, SEQ ID NO:27; SEQ ID NO:28; SEQ ID NO:29; SEQ ID NO:30; SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is modified with a non-ribose backbone, such as phosphorodiamidate morpholino. In embodiments, SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50 is a phosphorodiamidate morpholino modified oligonucleotide.

In embodiments, the oligonucleotide comprising a mirtron splice site binding sequence is an oligonucleotide comprising a nucleic acid sequence having at least 80% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 85% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 90% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 91% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 92% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 93% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 94% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 95% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 96% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 97% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 98% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40;

SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising a nucleic acid sequence having at least 99% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is an oligonucleotide comprising SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is at least 2 nucleic acids in length. In embodiments, the oligonucleotide comprising a mirtron splice site binding sequence is at least 3 nucleic acids in length. In embodiments, the oligonucleotide comprising a mirtron splice site binding sequence is at least 4 nucleic acids in length. In embodiments, the oligonucleotide comprising a mirtron splice site binding sequence is at least 5 nucleic acids in length. In embodiments, the oligonucleotide comprising a mirtron splice site binding sequence is at least 6 nucleic acids in length. In embodiments, the oligonucleotide comprising a mirtron splice site binding sequence is at least 7 nucleic acids in length. In embodiments, the oligonucleotide comprising a mirtron splice site binding sequence is at least 8 nucleic acids in length. In embodiments, the oligonucleotide comprising a mirtron splice site binding sequence is at least 9 nucleic acids in length. In embodiments, the oligonucleotide comprising a mirtron splice site binding sequence is at least 10 nucleic acids in length. In embodiments, the oligonucleotide comprising a mirtron splice site binding sequence is at least 11 nucleic acids in length. In embodiments, the oligonucleotide comprising a mirtron splice site binding sequence is at least 12 nucleic acids in length. In embodiments, the oligonucleotide comprising a mirtron splice site binding sequence is at least 13 nucleic acids in length. In embodiments, the oligonucleotide comprising a mirtron splice site binding sequence is at least 14 nucleic acids in length. In embodiments, the oligonucleotide comprising a mirtron splice site binding sequence is at least 15 nucleic acids in length. In embodiments, the oligonucleotide comprising a mirtron splice site binding sequence is at least 16 nucleic acids in length. In embodiments, the oligonucleotide comprising a mirtron splice site binding sequence is at least 17 nucleic acids in length. In embodiments, the oligonucleotide comprising a mirtron splice site binding sequence is at least 18 nucleic acids in length. In embodiments, the oligonucleotide comprising a mirtron splice site binding sequence is at least 19 nucleic acids in length. In embodiments, the oligonucleotide comprising a mirtron splice site binding sequence is at least 20 nucleic acids in length. In embodiments, the oligonucleotide comprising a mirtron splice site binding sequence is at least 21 nucleic acids in length. In embodiments, the oligonucleotide comprising a mirtron splice site binding sequence is at least 22 nucleic acids in length. In embodiments, the oligonucleotide comprising a mirtron splice site binding sequence is at least 23 nucleic acids in length. In embodiments, the oligonucleotide comprising a mirtron splice site binding sequence is at least 24 nucleic acids in length. In embodiments, the oligonucleotide comprising a mirtron splice site binding sequence is at least 25 nucleic acids in length. In embodiments, the oligonucleotide comprising a mirtron splice site binding sequence is at least 30 nucleic acids in length. In embodiments, the oligonucleotide comprising a mirtron splice site binding sequence is at least 35 nucleic acids in length. In embodiments, the oligonucleotide comprising a mirtron splice site binding sequence is at least 40 nucleic acids in length. Depending on the length of the mirtron splice site binding sequence, the mirtron splice site binding sequence may overlap with adjacent exon and/or intron sequences. In embodiments, the oligonucleotide comprising a mirtron splice site binding sequence comprises from about 10 nucleotides to about 50 nucleotides; or from about 15 nucleotides to about 40 nucleotides. Depending on the length of the mirtron splice site binding sequence, the mirtron splice site binding sequence may hybridize with adjacent exon and/or intron sequences in addition to hybridizing with the mirtron splice site sequence.

In embodiments, the kits further includes a cell. In embodiments, the cell is a bacterial cell. In embodiments, the cell is a eukaryotic cell. In embodiments, the cell is a T cell. In embodiments, the cell is a HT1080 or HEK293T cell. In embodiments, the cell is a HT1080. In embodiments, the cell is a HEK293T cell (also referred to as 293T).

Method

In an aspect is provided a method for producing a lentivirus. The method comprises the step of: transfecting a cell with: (i) a oligonucleotide comprising a mirtron splice site binding sequence, and (ii) a lentiviral packaging system; thereby producing the lentivirus.

In embodiments, the cell is a bacterial cell. In embodiments, the cell is a eukaryotic cell. In embodiments, the cell is a T cell. In embodiments, the cell is a HT1080 or HEK293T cell. In embodiments, the cell is a HT1080. In embodiments, the cell is a HEK293T cell (also referred to as 293T).2

In embodiments, the lentivirus is any known in the art, as defined and described herein. In embodiments, the lentivirus is a human immunodeficiency virus. In embodiments, the lentivirus is a pHIV7-EGFP lentivirus.

In embodiments, the lentiviral packaging system is a second generation lentiviral packaging system, as defined and described herein. In embodiments, the lentiviral packaging system is a third generation lentiviral packaging system, as defined and described herein.

In embodiments, an oligonucleotide comprising a mirtron splice site binding sequence is SEQ ID NO:3; SEQ ID NO:4; SEQ ID NO:5; SEQ ID NO:6; SEQ ID NO:7; SEQ ID NO:8;

SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is a nucleic acid that binds to a region of the MCMI splice donor site and comprises one of the following sequences: SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26.

In embodiments, the oligonucleotide comprising a mirtron splice site binding sequence is a nucleic acid that binds to a region of the MCMI splice acceptor site and comprises one of the following amino acid sequences: SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50

In embodiments, the oligonucleotide comprising a mirtron splice site binding sequence is a modified oligonucleotide. In embodiments, the oligonucleotide comprising a mirtron splice site binding sequence is a modified oligonucleotide of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the modified oligonucleotide is a 2'-O-methyl modified oligonucleotide. In embodiments, the modified oligonucleotide is a morpholino. In embodiments, the modified oligonucleotide is a LNA. In embodiments, the modified oligonucleotide includes a combination of LNA, 2'-O-methyl, and morpholino modified oligonucleotides. In embodiments, the oligonucleotide comprising a mirtron splice site binding sequence comprises at least one modified nucleic acid. In embodiments, the oligonucleotide comprising a mirtron splice site binding sequence comprises from 1 to about 20 modified nucleic acids; from 1 to about 15 modified nucleic acids; or from 1 to about 10 modified nucleic acids; or 1 to about 5 modified nucleic acids; or contains 1, 2, 3, 4, 5, 6, 7, 8, 9, 10, 11, 12, 13, 14, 15, 16, 17, 18, 19, 20, 21, 22, 23, or 24 modified nucleic acids.

In embodiments, the oligonucleotide comprising a mirtron splice site binding sequence is an oligonucleotide comprising a nucleic acid sequence having at least 80% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 85% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 90% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 91% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 92% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 93% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 94% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 95% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 96% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 97% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 98% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising a nucleic acid sequence having at least 99% sequence identity to SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50. In embodiments, the oligonucleotide comprising a mirtron splice site binding sequence is an oligonucleotide comprising SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30, SEQ ID NO:31; SEQ ID NO:32; SEQ ID NO:33; SEQ ID NO:34, SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; or SEQ ID NO:50.

In embodiments, the oligonucleotide comprising a mirtron splice site binding sequence is at least 2 nucleic acids in length. In embodiments, the oligonucleotide comprising a mirtron splice site binding sequence is at least 3 nucleic acids in length. In embodiments, the oligonucleotide comprising a mirtron splice site binding sequence is at least 4 nucleic acids in length. In embodiments, the oligonucleotide comprising a mirtron splice site binding sequence is at least 5 nucleic acids in length. In embodiments, the oligonucleotide comprising a mirtron splice site binding sequence is at least 6 nucleic acids in length. In embodiments, the oligonucleotide comprising a mirtron splice site binding sequence is at least 7 nucleic acids in length. In embodiments, the oligonucleotide comprising a mirtron splice site binding sequence is at least 8 nucleic acids in length. In embodiments, the oligonucleotide comprising a mirtron splice site binding sequence is at least 9 nucleic acids in length. In embodiments, the oligonucleotide comprising a mirtron splice site binding sequence is at least 10 nucleic acids in length. In embodiments, the oligonucleotide comprising a mirtron splice site binding sequence is at least 11 nucleic acids in length. In embodiments, the oligonucleotide comprising a mirtron splice site binding sequence is at least 12 nucleic acids in length. In embodiments, the oligonucleotide comprising a mirtron splice site binding sequence is at least 13 nucleic acids in length. In embodiments, the oligonucleotide comprising a mirtron splice site binding sequence is at least 14 nucleic acids in length. In embodiments, the oligonucleotide comprising a mirtron splice site binding sequence is at least 15 nucleic acids in length. In embodiments, the oligonucleotide comprising a mirtron splice site binding sequence is at least 16 nucleic acids in length. In embodiments, the oligonucleotide comprising a mirtron splice site binding sequence is at least 17 nucleic acids in length. In embodiments, the oligonucleotide comprising a mirtron splice site binding sequence is at least 18 nucleic acids in length. In embodiments, the oligonucleotide comprising a mirtron splice site binding sequence is at least 19 nucleic acids in length. In embodiments, the oligonucleotide comprising a mirtron splice site binding sequence is at least 20 nucleic acids in length. In embodiments, the oligonucleotide comprising a mirtron splice site binding sequence is at least 21 nucleic acids in length. In embodiments, the oligonucleotide comprising a mirtron splice site binding sequence is at least 22 nucleic acids in length. In embodiments, the oligonucleotide comprising a mirtron splice site binding sequence is at least 23 nucleic acids in length. In embodiments, the oligonucleotide comprising a mirtron splice site binding sequence is at least 24 nucleic acids in length. In embodiments, the oligonucleotide comprising a mirtron splice site binding sequence is at least 25 nucleic acids in length. In embodiments, the oligonucleotide comprising a mirtron splice site binding sequence is at least 30 nucleic acids in length. In embodiments, the oligonucleotide comprising a mirtron splice site binding sequence is at least 35 nucleic acids in length. In embodiments, the oligonucleotide comprising a mirtron splice site binding sequence is at least 40 nucleic acids in length. In embodiments, the oligonucleotide comprising a mirtron splice site binding sequence comprises from about 10 nucleotides to about 50 nucleotides; or from about 15 nucleotides to about 40 nucleotides. Depending on the length of the mirtron splice site binding sequence, the mirtron splice site binding sequence may hybridize with the mirtron splice site sequence including the adjacent exon and/or intron sequences.

EMBODIMENTS

Embodiment 1. A kit comprising: (i) an oligonucleotide comprising a mirtron splice site binding sequence; and (ii) a lentiviral packaging system.

Embodiment 2. The kit of Embodiment 1, wherein the lentiviral packaging system is a second generation lentiviral packaging system.

Embodiment 3. The kit of Embodiment 1, wherein the lentiviral packaging system is a third generation lentiviral packaging system.

Embodiment 4. The kit of any one of Embodiments 1 to 3, further comprising a cell.

Embodiment 5. The kit of Embodiment 4, wherein the cell is a bacterial cell.

Embodiment 6. The kit of Embodiment 4, wherein the cell is a eukaryotic cell.

Embodiment 7. The kit of Embodiment 4, wherein the cell is a T cell.

Embodiment 8. The kit of Embodiment 4, wherein the cell is HT1080.

Embodiment 9. The kit of Embodiment 4, wherein the cell is HEK293T.

Embodiment 10. The kit of any one of Embodiments 1 to 9, wherein the mirtron splice site binding sequence comprises: (i) a nucleic acid that binds to a region of the MCM7 splice donor site, or (ii) a nucleic acid that binds to a region of the MCM7 splice acceptor site.

Embodiment 11. A method for producing a lentivirus, the method comprising the step of: transfecting a cell with: (i) an oligonucleotide comprising a mirtron splice site binding sequence, and (ii) a lentiviral packaging system; thereby producing the lentivirus Embodiment 12. The method of Embodiment 11, wherein the cell is a bacterial cell.

Embodiment 13. The method of Embodiment 11, wherein the cell is a eukaryotic cell.

Embodiment 14. The method of Embodiment 11, wherein the cell is a T cell.

Embodiment 15. The method of Embodiment 11, wherein the cell is HT1080.

Embodiment 16. The method of Embodiment 11, wherein the cell is HEK293T.

Embodiment 17. The method of any one of Embodiments 11 to 16, wherein the lentivirus is a pHIV7-EGFP lentivirus.

Embodiment 18. The method of any one of Embodiments 11 to 17, wherein the lentiviral packaging system is a second generation lentiviral packaging system.

Embodiment 19. The method of any one of Embodiments 11 to 17, wherein the lentiviral packaging system is a third generation lentiviral packaging system.

Embodiment 20. The method of any one of Embodiments 11 to 18, wherein the mirtron splice site binding sequence comprises: (i) a nucleic acid that binds to a region of the MCM7 splice donor site, or (ii) a nucleic acid that binds to a region of the MCM7 splice acceptor site.

Embodiment 21. The kit of any one of Embodiments 1-10 or the method of any one of Embodiments 11-20, wherein the oligonucleotide comprises a nucleic acid sequence having at least 80% sequence identity to SEQ ID NO:3. The kit of any one of Embodiments 1-10 or the method of any one of Embodiments 11-20, wherein the oligonucleotide comprises a nucleic acid sequence having at least 80% sequence identity to SEQ ID NO:4. The kit of any one of Embodiments 1-10 or the method of any one of Embodiments 11-20, wherein the oligonucleotide comprises a nucleic acid sequence having at least 80% sequence identity to SEQ ID NO:5. The kit of any one of Embodiments 1-10 or the method of any one of Embodiments 11-20, wherein the oligonucleotide comprises a nucleic acid sequence having at least 80% sequence identity to SEQ ID NO:6. The kit of any one of Embodiments 1-10 or the method of any one of Embodiments 11-20, wherein the oligonucleotide comprises a nucleic acid sequence having at least 80% sequence identity to SEQ ID NO:7. The kit of any one of Embodiments 1-10 or the method of any one of Embodiments 11-20, wherein the oligonucleotide comprises a nucleic acid sequence having at least 80% sequence identity to SEQ ID NO:8. The kit of any one of Embodiments 1-10 or the method of any one of Embodiments 11-20, wherein the oligonucleotide comprises a nucleic acid sequence having at least 80% sequence identity to SEQ ID NO:9. The kit of any one of Embodiments 1-10 or the method of any one of Embodiments 11-20, wherein the oligonucleotide comprises a nucleic acid sequence having at least 80% sequence identity to SEQ ID NO:10. The kit of any one of Embodiments 1-10 or the method of any one of Embodiments 11-20, wherein the oligonucleotide comprises a nucleic acid sequence having at least 80% sequence identity to SEQ ID NO:11. The kit of any one of Embodiments 1-10 or the method of any one of Embodiments 11-20, wherein the oligonucleotide comprises a nucleic acid sequence having at least 80% sequence identity to SEQ ID NO:12. The kit of any one of Embodiments 1-10 or the method of any one of Embodiments 11-20, wherein the oligonucleotide comprises a nucleic acid sequence having at least 80% sequence identity to SEQ ID NO:13. The kit of any one of Embodiments 1-10 or the method of any one of Embodiments 11-20, wherein the oligonucleotide comprises a nucleic acid sequence having at least 80% sequence identity to SEQ ID NO:14. The kit of any one of Embodiments 1-10 or the method of any one of Embodiments 11-20, wherein the oligonucleotide comprises a nucleic acid sequence having at least 80% sequence identity to SEQ ID NO:15. The kit of any one of Embodiments 1-10 or the method of any one of Embodiments 11-20, wherein the oligonucleotide comprises a nucleic acid sequence having at least 80% sequence identity to SEQ ID NO:16. The kit of any one of Embodiments 1-10 or the method of any one of Embodiments 11-20, wherein the oligonucleotide comprises a nucleic acid sequence having at least 80% sequence identity to SEQ ID NO:17. The kit of any one of Embodiments 1-10 or the method of any one of Embodiments 11-20, wherein the oligonucleotide comprises a nucleic acid sequence having at least 80% sequence identity to SEQ ID NO:18. The kit of any one of Embodiments 1-10 or the method of any one of Embodiments 11-20, wherein the oligonucleotide comprises a nucleic acid sequence having at least 80% sequence identity to SEQ ID NO:19. The kit of any one of Embodiments 1-10 or the method of any one of Embodiments 11-20, wherein the oligonucleotide comprises a nucleic acid sequence having at least 80% sequence identity to SEQ ID NO:20. The kit of any one of Embodiments 1-10 or the method of any one of Embodiments 11-20, wherein the oligonucleotide comprises a nucleic acid sequence having at least 80% sequence identity to SEQ ID NO:21. The kit of any one of Embodiments 1-10 or the method of any one of Embodiments 11-20, wherein the oligonucleotide comprises a nucleic acid sequence having at least 80% sequence identity to SEQ ID NO:22. The kit of any one of Embodiments 1-10 or the method of any one of Embodiments 11-20, wherein the oligonucleotide comprises a nucleic acid sequence having at least 80% sequence identity to SEQ ID NO:23. The kit of any one of Embodiments 1-10 or the method of any one of Embodiments 11-20, wherein the oligonucleotide comprises a nucleic acid sequence having at least 80% sequence identity to SEQ ID NO:24. The kit of any one of Embodiments 1-10 or the method of any one of Embodiments 11-20, wherein the oligonucleotide comprises a nucleic acid sequence having at least 80% sequence identity to SEQ ID NO:25. The kit of any one of Embodiments 1-10 or the method of any one of Embodiments 11-20, wherein the oligonucleotide comprises a nucleic acid sequence having at least 80% sequence identity to SEQ ID NO:26. The kit of any one of Embodiments 1-10 or the method of any one of Embodiments 11-20, wherein the oligonucleotide comprises a nucleic acid sequence having at least 80% sequence identity to SEQ ID NO:27. The kit of any one of Embodiments 1-10 or the method of any one of Embodiments 11-20, wherein the oligonucleotide comprises a nucleic acid sequence having at least 80% sequence identity to SEQ ID NO:28. The kit of any one of Embodiments 1-10 or the method of any one of Embodiments 11-20, wherein the oligonucleotide comprises a nucleic acid sequence having at least 80% sequence identity to SEQ ID NO:29. The kit of any one of Embodiments 1-10 or the method of any one of Embodiments 11-20, wherein the oligonucleotide comprises a nucleic acid sequence having at least 80% sequence identity to SEQ ID NO:30. The kit of any one of Embodiments 1-10 or the method of any one of Embodiments 11-20, wherein the oligonucleotide comprises a nucleic acid sequence having at least 80% sequence identity to SEQ ID NO:31. The kit of any one of Embodiments 1-10 or the method of any one of Embodiments 11-20, wherein the oligonucleotide comprises a nucleic acid sequence having at least 80% sequence identity to SEQ ID NO:32. The kit of any one of Embodiments 1-10 or the method of any one of Embodiments 11-20, wherein the oligonucleotide comprises a nucleic acid sequence having at least 80% sequence identity to SEQ ID NO:33. The kit of any one of Embodiments 1-10 or the method of any one of Embodiments 11-20, wherein the oligonucleotide comprises a nucleic acid sequence having at least 80% sequence identity to SEQ ID NO:34. The kit of any one of Embodiments 1-10 or the method of any one of Embodiments 11-20, wherein the oligonucleotide comprises a nucleic acid sequence having at least 80% sequence identity to SEQ ID NO:35. The kit of any one of Embodiments 1-10 or the method of any one of Embodiments 11-20, wherein the oligonucleotide comprises a nucleic acid sequence having at least 80% sequence identity to SEQ ID NO:36. The kit of any one of Embodiments 1-10 or the method of any one of Embodiments 11-20, wherein the oligonucleotide comprises a nucleic acid sequence having at least 80% sequence identity to SEQ ID NO:37. The kit of any one of Embodiments 1-10 or the method of any one of Embodiments 11-20, wherein the oligonucleotide comprises a nucleic acid sequence having at least 80% sequence identity to SEQ ID NO:38. The kit of any one of Embodiments 1-10 or the method of any one of Embodiments 11-20, wherein the oligonucleotide comprises a nucleic acid sequence having at least 80% sequence identity to SEQ ID NO:39. The kit of any one of Embodiments 1-10 or the method of any one of Embodiments 11-20, wherein the oligonucleotide comprises a nucleic acid sequence having at least 80% sequence identity to SEQ ID NO:40. The kit of any one of Embodiments 1-10 or the method of any one of Embodiments 11-20, wherein the oligonucleotide comprises a nucleic acid sequence having at least 80% sequence identity to SEQ ID NO:41. The kit of any one of Embodiments 1-10 or the method of any one of Embodiments 11-20, wherein the oligonucleotide comprises a nucleic acid sequence having at least 80% sequence identity to SEQ ID NO:42. The kit of any one of Embodiments 1-10 or the method of any one of Embodiments 11-20, wherein the oligonucleotide comprises a nucleic acid sequence having at least 80% sequence identity to SEQ ID NO:43. The kit of any one of Embodiments 1-10 or the method of any one of Embodiments 11-20, wherein the oligonucleotide comprises a nucleic acid sequence having at least 80% sequence identity to SEQ ID NO:44. The kit of any one of Embodiments 1-10 or the method of any one of Embodiments 11-20, wherein the oligonucleotide comprises a nucleic acid sequence having at least 80% sequence identity to SEQ ID NO:45. The kit of any one of Embodiments 1-10 or the method of any one of Embodiments 11-20, wherein the oligonucleotide comprises a nucleic acid sequence having at least 80% sequence identity to SEQ ID NO:46. The kit of any one of Embodiments 1-10 or the method of any one of Embodiments 11-20, wherein the oligonucleotide comprises a nucleic acid sequence having at least 80% sequence identity to SEQ ID NO:47. The kit of any one of Embodiments 1-10 or the method of any one of Embodiments 11-20, wherein the oligonucleotide comprises a nucleic acid sequence having at least 80% sequence identity to SEQ ID NO:48. The kit of any one of Embodiments 1-10 or the method of any one of Embodiments 11-20, wherein the oligonucleotide comprises a nucleic acid sequence having at least 80% sequence identity to SEQ ID NO:49. The kit of any one of Embodiments 1-10 or the method of any one of Embodiments 11-20, wherein the oligonucleotide comprises a nucleic acid sequence having at least 80% sequence identity to SEQ ID NO:50.

Embodiment 22. The kit of any one of Embodiments 1-10 or the method of any one of Embodiments 11-20, wherein the oligonucleotide comprises a nucleic acid sequence having at least 85% sequence identity to SEQ ID NO:3. The kit of any one of Embodiments 1-10 or the method of any one of Embodiments 11-20, wherein the oligonucleotide comprises a nucleic acid sequence having at least 85% sequence identity to SEQ ID NO:4. The kit of any one of Embodiments 1-10 or the method of any one of Embodiments 11-20, wherein the oligonucleotide comprises a nucleic acid sequence having at least 85% sequence identity to SEQ ID NO:5. The kit of any one of Embodiments 1-10 or the method of any one of Embodiments 11-20, wherein the oligonucleotide comprises a nucleic acid sequence having at least 85% sequence identity to SEQ ID NO:6. The kit of any one of Embodiments 1-10 or the method of any one of Embodiments 11-20, wherein the oligonucleotide comprises a nucleic acid sequence having at least 85% sequence identity to SEQ ID NO:7. The kit of any one of Embodiments 1-10 or the method of any one of Embodiments 11-20, wherein the oligonucleotide comprises a nucleic acid sequence having at least 85% sequence identity to SEQ ID NO:8. The kit of any one of Embodiments 1-10 or the method of any one of Embodiments 11-20, wherein the oligonucleotide comprises a nucleic acid sequence having at least 85% sequence identity to SEQ ID NO:9. The kit of any one of Embodiments 1-10 or the method of any one of Embodiments 11-20, wherein the oligonucleotide comprises a nucleic acid sequence having at least 85% sequence identity to SEQ ID NO:10. The kit of any one of Embodiments 1-10 or the method of any one of Embodiments 11-20, wherein the oligonucleotide comprises a nucleic acid sequence having at least 85% sequence identity to SEQ ID NO:11. The kit of any one of Embodiments 1-10 or the method of any one of Embodiments 11-20, wherein the oligonucleotide comprises a nucleic acid sequence having at least 85% sequence identity to SEQ ID NO:12. The kit of any one of Embodiments 1-10 or the method of any one of Embodiments 11-20, wherein the oligonucleotide comprises a nucleic acid sequence having at least 85% sequence identity to SEQ ID NO:13. The kit of any one of Embodiments 1-10 or the method of any one of Embodiments 11-20, wherein the oligonucleotide comprises a nucleic acid sequence having at least 85% sequence identity to SEQ ID NO:14. The kit of any one of Embodiments 1-10 or the method of any one of Embodiments 11-20, wherein the oligonucleotide comprises a nucleic acid sequence having at least 85% sequence identity to SEQ ID NO:15. The kit of any one of Embodiments 1-10 or the method of any one of Embodiments 11-20, wherein the oligonucleotide comprises a nucleic acid sequence having at least 85% sequence identity to SEQ ID NO:16. The kit of any one of Embodiments 1-10 or the method of any one of Embodiments 11-20, wherein the oligonucleotide comprises a nucleic acid sequence having at least 85% sequence identity to SEQ ID NO:17. The kit of any one of Embodiments 1-10 or the method of any one of Embodiments 11-20, wherein the oligonucleotide comprises a nucleic acid sequence having at least 85% sequence identity to SEQ ID NO:18. The kit of any one of Embodiments 1-10 or the method of any one of Embodiments 11-20, wherein the oligonucleotide comprises a nucleic acid sequence having at least 85% sequence identity to SEQ ID NO:19. The kit of any one of Embodiments 1-10 or the method of any one of Embodiments 11-20, wherein the oligonucleotide comprises a nucleic acid sequence having at least 85% sequence identity to SEQ ID NO:20. The kit of any one of Embodiments 1-10 or the method of any one of Embodiments 11-20, wherein the oligonucleotide comprises a nucleic acid sequence having at least 85% sequence identity to SEQ ID NO:21. The kit of any one of Embodiments 1-10 or the method of any one of Embodiments 11-20, wherein the oligonucleotide comprises a nucleic acid sequence having at least 85% sequence identity to SEQ ID NO:22. The kit of any one of Embodiments 1-10 or the method of any one of Embodiments 11-20, wherein the oligonucleotide comprises a nucleic acid sequence having at least 85% sequence identity to SEQ ID NO:23. The kit of any one of Embodiments 1-10 or the method of any one of Embodiments 11-20, wherein the oligonucleotide comprises a nucleic acid sequence having at least 85% sequence identity to SEQ ID NO:24. The kit of any one of Embodiments 1-10 or the method of any one of Embodiments 11-20, wherein the oligonucleotide comprises a nucleic acid sequence having at least 85% sequence identity to SEQ ID NO:25. The kit of any one of Embodiments 1-10 or the method of any one of Embodiments 11-20, wherein the oligonucleotide comprises a nucleic acid sequence having at least 85% sequence identity to SEQ ID NO:26. The kit of any one of Embodiments 1-10 or the method of any one of Embodiments 11-20, wherein the oligonucleotide comprises a nucleic acid sequence having at least 85% sequence identity to SEQ ID NO:27. The kit of any one of Embodiments 1-10 or the method of any one of Embodiments 11-20, wherein the oligonucleotide comprises a nucleic acid sequence having at least 85% sequence identity to SEQ ID NO:28. The kit of any one of Embodiments 1-10 or the method of any one of Embodiments 11-20, wherein the oligonucleotide comprises a nucleic acid sequence having at least 85% sequence identity to SEQ ID NO:29. The kit of any one of Embodiments 1-10 or the method of any one of Embodiments 11-20, wherein the oligonucleotide comprises a nucleic acid sequence having at least 85% sequence identity to SEQ ID NO:30. The kit of any one of Embodiments 1-10 or the method of any one of Embodiments 11-20, wherein the oligonucleotide comprises a nucleic acid sequence having at least 85% sequence identity to SEQ ID NO:31. The kit of any one of Embodiments 1-10 or the method of any one of Embodiments 11-20, wherein the oligonucleotide comprises a nucleic acid sequence having at least 85% sequence identity to SEQ ID NO:32. The kit of any one of Embodiments 1-10 or the method of any one of Embodiments 11-20, wherein the oligonucleotide comprises a nucleic acid sequence having at least 85% sequence identity to SEQ ID NO:33. The kit of any one of Embodiments 1-10 or the method of any one of Embodiments 11-20, wherein the oligonucleotide comprises a nucleic acid sequence having at least 85% sequence identity to SEQ ID NO:34. The kit of any one of Embodiments 1-10 or the method of any one of Embodiments 11-20, wherein the oligonucleotide comprises a nucleic acid sequence having at least 85% sequence identity to SEQ ID NO:35. The kit of any one of Embodiments 1-10 or the method of any one of Embodiments 11-20, wherein the oligonucleotide comprises a nucleic acid sequence having at least 85% sequence identity to SEQ ID NO:36. The kit of any one of Embodiments 1-10 or the method of any one of Embodiments 11-20, wherein the oligonucleotide comprises a nucleic acid sequence having at least 85% sequence identity to SEQ ID NO:37. The kit of any one of Embodiments 1-10 or the method of any one of Embodiments 11-20, wherein the oligonucleotide comprises a nucleic acid sequence having at least 85% sequence identity to SEQ ID NO:38. The kit of any one of Embodiments 1-10 or the method of any one of Embodiments 11-20, wherein the oligonucleotide comprises a nucleic acid sequence having at least 85% sequence identity to SEQ ID NO:39. The kit of any one of Embodiments 1-10 or the method of any one of Embodiments 11-20, wherein the oligonucleotide comprises a nucleic acid sequence having at least 85% sequence identity to SEQ ID NO:40. The kit of any one of Embodiments 1-10 or the method of any one of Embodiments 11-20, wherein the oligonucleotide comprises a nucleic acid sequence having at least 85% sequence identity to SEQ ID NO:41. The kit of any one of Embodiments 1-10 or the method of any one of Embodiments 11-20, wherein the oligonucleotide comprises a nucleic acid sequence having at least 85% sequence identity to SEQ ID NO:42. The kit of any one of Embodiments 1-10 or the method of any one of Embodiments 11-20, wherein the oligonucleotide comprises a nucleic acid sequence having at least 85% sequence identity to SEQ ID NO:43. The kit of any one of Embodiments 1-10 or the method of any one of Embodiments 11-20, wherein the oligonucleotide comprises a nucleic acid sequence having at least 85% sequence identity to SEQ ID NO:44. The kit of any one of Embodiments 1-10 or the method of any one of Embodiments 11-20, wherein the oligonucleotide comprises a nucleic acid sequence having at least 85% sequence identity to SEQ ID NO:45. The kit of any one of Embodiments 1-10 or the method of any one of Embodiments 11-20, wherein the oligonucleotide comprises a nucleic acid sequence having at least 85% sequence identity to SEQ ID NO:46. The kit of any one of Embodiments 1-10 or the method of any one of Embodiments 11-20, wherein the oligonucleotide comprises a nucleic acid sequence having at least 85% sequence identity to SEQ ID NO:47. The kit of any one of Embodiments 1-10 or the method of any one of Embodiments 11-20, wherein the oligonucleotide comprises a nucleic acid sequence having at least 85% sequence identity to SEQ ID NO:48. The kit of any one of Embodiments 1-10 or the method of any one of Embodiments 11-20, wherein the oligonucleotide comprises a nucleic acid sequence having at least 85% sequence identity to SEQ ID NO:49. The kit of any one of Embodiments 1-10 or the method of any one of Embodiments 11-20, wherein the oligonucleotide comprises a nucleic acid sequence having at least 85% sequence identity to SEQ ID NO:50.

Embodiment 23. The kit of any one of Embodiments 1-10 or the method of any one of Embodiments 11-20, wherein the oligonucleotide comprises a nucleic acid sequence having at least 90% sequence identity to SEQ ID NO:3. The kit of any one of Embodiments 1-10 or the method of any one of Embodiments 11-20, wherein the oligonucleotide comprises a nucleic acid sequence having at least 90% sequence identity to SEQ ID NO:4. The kit of any one of Embodiments 1-10 or the method of any one of Embodiments 11-20, wherein the oligonucleotide comprises a nucleic acid sequence having at least 90% sequence identity to SEQ ID NO:5. The kit of any one of Embodiments 1-10 or the method of any one of Embodiments 11-20, wherein the oligonucleotide comprises a nucleic acid sequence having at least 90% sequence identity to SEQ ID NO:6. The kit of any one of Embodiments 1-10 or the method of any one of Embodiments 11-20, wherein the oligonucleotide comprises a nucleic acid sequence having at least 90% sequence identity to SEQ ID NO:7. The kit of any one of Embodiments 1-10 or the method of any one of Embodiments 11-20, wherein the oligonucleotide comprises a nucleic acid sequence having at least 90% sequence identity to SEQ ID NO:8. The kit of any one of Embodiments 1-10 or the method of any one of Embodiments 11-20, wherein the oligonucleotide comprises a nucleic acid sequence having at least 90% sequence identity to SEQ ID NO:9. The kit of any one of Embodiments 1-10 or the method of any one of Embodiments 11-20, wherein the oligonucleotide comprises a nucleic acid sequence having at least 90% sequence identity to SEQ ID NO:10. The kit of any one of Embodiments 1-10 or the method of any one of Embodiments 11-20, wherein the oligonucleotide comprises a nucleic acid sequence having at least 90% sequence identity to SEQ ID NO:11. The kit of any one of Embodiments 1-10 or the method of any one of Embodiments 11-20, wherein the oligonucleotide comprises a nucleic acid sequence having at least 90% sequence identity to SEQ ID NO:12. The kit of any one of Embodiments 1-10 or the method of any one of Embodiments 11-20, wherein the oligonucleotide comprises a nucleic acid sequence having at least 90% sequence identity to SEQ ID NO:13. The kit of any one of Embodiments 1-10 or the method of any one of Embodiments 11-20, wherein the oligonucleotide comprises a nucleic acid sequence having at least 90% sequence identity to SEQ ID NO:14. The kit of any one of Embodiments 1-10 or the method of any one of Embodiments 11-20, wherein the oligonucleotide comprises a nucleic acid sequence having at least 90% sequence identity to SEQ ID NO:15. The kit of any one of Embodiments 1-10 or the method of any one of Embodiments 11-20, wherein the oligonucleotide comprises a nucleic acid sequence having at least 90% sequence identity to SEQ ID NO:16. The kit of any one of Embodiments 1-10 or the method of any one of Embodiments 11-20, wherein the oligonucleotide comprises a nucleic acid sequence having at least 90% sequence identity to SEQ ID NO:17. The kit of any one of Embodiments 1-10 or the method of any one of Embodiments 11-20, wherein the oligonucleotide comprises a nucleic acid sequence having at least 90% sequence identity to SEQ ID NO:18. The kit of any one of Embodiments 1-10 or the method of any one of Embodiments 11-20, wherein the oligonucleotide comprises a nucleic acid sequence having at least 90% sequence identity to SEQ ID NO:19. The kit of any one of Embodiments 1-10 or the method of any one of Embodiments 11-20, wherein the oligonucleotide comprises a nucleic acid sequence having at least 90% sequence identity to SEQ ID NO:20. The kit of any one of Embodiments 1-10 or the method of any one of Embodiments 11-20, wherein the oligonucleotide comprises a nucleic acid sequence having at least 90% sequence identity to SEQ ID NO:21. The kit of any one of Embodiments 1-10 or the method of any one of Embodiments 11-20, wherein the oligonucleotide comprises a nucleic acid sequence having at least 90% sequence identity to SEQ ID NO:22. The kit of any one of Embodiments 1-10 or the method of any one of Embodiments 11-20, wherein the oligonucleotide comprises a nucleic acid sequence having at least 90% sequence identity to SEQ ID NO:23. The kit of any one of Embodiments 1-10 or the method of any one of Embodiments 11-20, wherein the oligonucleotide comprises a nucleic acid sequence having at least 90% sequence identity to SEQ ID NO:24. The kit of any one of Embodiments 1-10 or the method of any one of Embodiments 11-20, wherein the oligonucleotide comprises a nucleic acid sequence having at least 90% sequence identity to SEQ ID NO:25. The kit of any one of Embodiments 1-10 or the method of any one of Embodiments 11-20, wherein the oligonucleotide comprises a nucleic acid sequence having at least 90% sequence identity to SEQ ID NO:26. The kit of any one of Embodiments 1-10 or the method of any one of Embodiments 11-20, wherein the oligonucleotide comprises a nucleic acid sequence having at least 90% sequence identity to SEQ ID NO:27. The kit of any one of Embodiments 1-10 or the method of any one of Embodiments 11-20, wherein the oligonucleotide comprises a nucleic acid sequence having at least 90% sequence identity to SEQ ID NO:28. The kit of any one of Embodiments 1-10 or the method of any one of Embodiments 11-20, wherein the oligonucleotide comprises a nucleic acid sequence having at least 90% sequence identity to SEQ ID NO:29. The kit of any one of Embodiments 1-10 or the method of any one of Embodiments 11-20, wherein the oligonucleotide comprises a nucleic acid sequence having at least 90% sequence identity to SEQ ID NO:30. The kit of any one of Embodiments 1-10 or the method of any one of Embodiments 11-20, wherein the oligonucleotide comprises a nucleic acid sequence having at least 90% sequence identity to SEQ ID NO:31. The kit of any one of Embodiments 1-10 or the method of any one of Embodiments 11-20, wherein the oligonucleotide comprises a nucleic acid sequence having at least 90% sequence identity to SEQ ID NO:32. The kit of any one of Embodiments 1-10 or the method of any one of Embodiments 11-20, wherein the oligonucleotide comprises a nucleic acid sequence having at least 90% sequence identity to SEQ ID NO:33. The kit of any one of Embodiments 1-10 or the method of any one of Embodiments 11-20, wherein the oligonucleotide comprises a nucleic acid sequence having at least 90% sequence identity to SEQ ID NO:34. The kit of any one of Embodiments 1-10 or the method of any one of Embodiments 11-20, wherein the oligonucleotide comprises a nucleic acid sequence having at least 90% sequence identity to SEQ ID NO:35. The kit of any one of Embodiments 1-10 or the method of any one of Embodiments 11-20, wherein the oligonucleotide comprises a nucleic acid sequence having at least 90% sequence identity to SEQ ID NO:36. The kit of any one of Embodiments 1-10 or the method of any one of Embodiments 11-20, wherein the oligonucleotide comprises a nucleic acid sequence having at least 90% sequence identity to SEQ ID NO:37. The kit of any one of Embodiments 1-10 or the method of any one of Embodiments 11-20, wherein the oligonucleotide comprises a nucleic acid sequence having at least 90% sequence identity to SEQ ID NO:38. The kit of any one of Embodiments 1-10 or the method of any one of Embodiments 11-20, wherein the oligonucleotide comprises a nucleic acid sequence having at least 90% sequence identity to SEQ ID NO:39. The kit of any one of Embodiments 1-10 or the method of any one of Embodiments 11-20, wherein the oligonucleotide comprises a nucleic acid sequence having at least 90% sequence identity to SEQ ID NO:40. The kit of any one of Embodiments 1-10 or the method of any one of Embodiments 11-20, wherein the oligonucleotide comprises a nucleic acid sequence having at least 90% sequence identity to SEQ ID NO:41. The kit of any one of Embodiments 1-10 or the method of any one of Embodiments 11-20, wherein the oligonucleotide comprises a nucleic acid sequence having at least 90% sequence identity to SEQ ID NO:42. The kit of any one of Embodiments 1-10 or the method of any one of Embodiments 11-20, wherein the oligonucleotide comprises a nucleic acid sequence having at least 90% sequence identity to SEQ ID NO:43. The kit of any one of Embodiments 1-10 or the method of any one of Embodiments 11-20, wherein the oligonucleotide comprises a nucleic acid sequence having at least 90% sequence identity to SEQ ID NO:44. The kit of any one of Embodiments 1-10 or the method of any one of Embodiments 11-20, wherein the oligonucleotide comprises a nucleic acid sequence having at least 90% sequence identity to SEQ ID NO:45. The kit of any one of Embodiments 1-10 or the method of any one of Embodiments 11-20, wherein the oligonucleotide comprises a nucleic acid sequence having at least 90% sequence identity to SEQ ID NO:46. The kit of any one of Embodiments 1-10 or the method of any one of Embodiments 11-20, wherein the oligonucleotide comprises a nucleic acid sequence having at least 90% sequence identity to SEQ ID NO:47. The kit of any one of Embodiments 1-10 or the method of any one of Embodiments 11-20, wherein the oligonucleotide comprises a nucleic acid sequence having at least 90% sequence identity to SEQ ID NO:48. The kit of any one of Embodiments 1-10 or the method of any one of Embodiments 11-20, wherein the oligonucleotide comprises a nucleic acid sequence having at least 90% sequence identity to SEQ ID NO:49. The kit of any one of Embodiments 1-10 or the method of any one of Embodiments 11-20, wherein the oligonucleotide comprises a nucleic acid sequence having at least 90% sequence identity to SEQ ID NO:50.

Embodiment 24. The kit of any one of Embodiments 1-10 or the method of any one of Embodiments 11-20, wherein the oligonucleotide comprises a nucleic acid sequence having at least 95% sequence identity to SEQ ID NO:3. The kit of any one of Embodiments 1-10 or the method of any one of Embodiments 11-20, wherein the oligonucleotide comprises a nucleic acid sequence having at least 95% sequence identity to SEQ ID NO:4. The kit of any one of Embodiments 1-10 or the method of any one of Embodiments 11-20, wherein the oligonucleotide comprises a nucleic acid sequence having at least 95% sequence identity to SEQ ID NO:5. The kit of any one of Embodiments 1-10 or the method of any one of Embodiments 11-20, wherein the oligonucleotide comprises a nucleic acid sequence having at least 95% sequence identity to SEQ ID NO:6. The kit of any one of Embodiments 1-10 or the method of any one of Embodiments 11-20, wherein the oligonucleotide comprises a nucleic acid sequence having at least 95% sequence identity to SEQ ID NO:7. The kit of any one of Embodiments 1-10 or the method of any one of Embodiments 11-20, wherein the oligonucleotide comprises a nucleic acid sequence having at least 95% sequence identity to SEQ ID NO:8. The kit of any one of Embodiments 1-10 or the method of any one of Embodiments 11-20, wherein the oligonucleotide comprises a nucleic acid sequence having at least 95% sequence identity to SEQ ID NO:9. The kit of any one of Embodiments 1-10 or the method of any one of Embodiments 11-20, wherein the oligonucleotide comprises a nucleic acid sequence having at least 95% sequence identity to SEQ ID NO:10. The kit of any one of Embodiments 1-10 or the method of any one of Embodiments 11-20, wherein the oligonucleotide comprises a nucleic acid sequence having at least 95% sequence identity to SEQ ID NO:11. The kit of any one of Embodiments 1-10 or the method of any one of Embodiments 11-20, wherein the oligonucleotide comprises a nucleic acid sequence having at least 95% sequence identity to SEQ ID NO:12. The kit of any one of Embodiments 1-10 or the method of any one of Embodiments 11-20, wherein the oligonucleotide comprises a nucleic acid sequence having at least 95% sequence identity to SEQ ID NO:13. The kit of any one of Embodiments 1-10 or the method of any one of Embodiments 11-20, wherein the oligonucleotide comprises a nucleic acid sequence having at least 95% sequence identity to SEQ ID NO:14. The kit of any one of Embodiments 1-10 or the method of any one of Embodiments 11-20, wherein the oligonucleotide comprises a nucleic acid sequence having at least 95% sequence identity to SEQ ID NO:15. The kit of any one of Embodiments 1-10 or the method of any one of Embodiments 11-20, wherein the oligonucleotide comprises a nucleic acid sequence having at least 95% sequence identity to SEQ ID NO:16. The kit of any one of Embodiments 1-10 or the method of any one of Embodiments 11-20, wherein the oligonucleotide comprises a nucleic acid sequence having at least 95% sequence identity to SEQ ID NO:17. The kit of any one of Embodiments 1-10 or the method of any one of Embodiments 11-20, wherein the oligonucleotide comprises a nucleic acid sequence having at least 95% sequence identity to SEQ ID NO:18. The kit of any one of Embodiments 1-10 or the method of any one of Embodiments 11-20, wherein the oligonucleotide comprises a nucleic acid sequence having at least 95% sequence identity to SEQ ID NO:19. The kit of any one of Embodiments 1-10 or the method of any one of Embodiments 11-20, wherein the oligonucleotide comprises a nucleic acid sequence having at least 95% sequence identity to SEQ ID NO:20. The kit of any one of Embodiments 1-10 or the method of any one of Embodiments 11-20, wherein the oligonucleotide comprises a nucleic acid sequence having at least 95% sequence identity to SEQ ID NO:21. The kit of any one of Embodiments 1-10 or the method of any one of Embodiments 11-20, wherein the oligonucleotide comprises a nucleic acid sequence having at least 95% sequence identity to SEQ ID NO:22. The kit of any one of Embodiments 1-10 or the method of any one of Embodiments 11-20, wherein the oligonucleotide comprises a nucleic acid sequence having at least 95% sequence identity to SEQ ID NO:23. The kit of any one of Embodiments 1-10 or the method of any one of Embodiments 11-20, wherein the oligonucleotide comprises a nucleic acid sequence having at least 95% sequence identity to SEQ ID NO:24. The kit of any one of Embodiments 1-10 or the method of any one of Embodiments 11-20, wherein the oligonucleotide comprises a nucleic acid sequence having at least 95% sequence identity to SEQ ID NO:25. The kit of any one of Embodiments 1-10 or the method of any one of Embodiments 11-20, wherein the oligonucleotide comprises a nucleic acid sequence having at least 95% sequence identity to SEQ ID NO:26. The kit of any one of Embodiments 1-10 or the method of any one of Embodiments 11-20, wherein the oligonucleotide comprises a nucleic acid sequence having at least 95% sequence identity to SEQ ID NO:27. The kit of any one of Embodiments 1-10 or the method of any one of Embodiments 11-20, wherein the oligonucleotide comprises a nucleic acid sequence having at least 95% sequence identity to SEQ ID NO:28. The kit of any one of Embodiments 1-10 or the method of any one of Embodiments 11-20, wherein the oligonucleotide comprises a nucleic acid sequence having at least 95% sequence identity to SEQ ID NO:29. The kit of any one of Embodiments 1-10 or the method of any one of Embodiments 11-20, wherein the oligonucleotide comprises a nucleic acid sequence having at least 95% sequence identity to SEQ ID NO:30. The kit of any one of Embodiments 1-10 or the method of any one of Embodiments 11-20, wherein the oligonucleotide comprises a nucleic acid sequence having at least 95% sequence identity to SEQ ID NO:31. The kit of any one of Embodiments 1-10 or the method of any one of Embodiments 11-20, wherein the oligonucleotide comprises a nucleic acid sequence having at least 95% sequence identity to SEQ ID NO:32. The kit of any one of Embodiments 1-10 or the method of any one of Embodiments 11-20, wherein the oligonucleotide comprises a nucleic acid sequence having at least 95% sequence identity to SEQ ID NO:33. The kit of any one of Embodiments 1-10 or the method of any one of Embodiments 11-20, wherein the oligonucleotide comprises a nucleic acid sequence having at least 95% sequence identity to SEQ ID NO:34. The kit of any one of Embodiments 1-10 or the method of any one of Embodiments 11-20, wherein the oligonucleotide comprises a nucleic acid sequence having at least 95% sequence identity to SEQ ID NO:35. The kit of any one of Embodiments 1-10 or the method of any one of Embodiments 11-20, wherein the oligonucleotide comprises a nucleic acid sequence having at least 95% sequence identity to SEQ ID NO:36. The kit of any one of Embodiments 1-10 or the method of any one of Embodiments 11-20, wherein the oligonucleotide comprises a nucleic acid sequence having at least 95% sequence identity to SEQ ID NO:37. The kit of any one of Embodiments 1-10 or the method of any one of Embodiments 11-20, wherein the oligonucleotide comprises a nucleic acid sequence having at least 95% sequence identity to SEQ ID NO:38. The kit of any one of Embodiments 1-10 or the method of any one of Embodiments 11-20, wherein the oligonucleotide comprises a nucleic acid sequence having at least 95% sequence identity to SEQ ID NO:39. The kit of any one of Embodiments 1-10 or the method of any one of Embodiments 11-20, wherein the oligonucleotide comprises a nucleic acid sequence having at least 95% sequence identity to SEQ ID NO:40. The kit of any one of Embodiments 1-10 or the method of any one of Embodiments 11-20, wherein the oligonucleotide comprises a nucleic acid sequence having at least 95% sequence identity to SEQ ID NO:41. The kit of any one of Embodiments 1-10 or the method of any one of Embodiments 11-20, wherein the oligonucleotide comprises a nucleic acid sequence having at least 95% sequence identity to SEQ ID NO:42. The kit of any one of Embodiments 1-10 or the method of any one of Embodiments 11-20, wherein the oligonucleotide comprises a nucleic acid sequence having at least 95% sequence identity to SEQ ID NO:43. The kit of any one of Embodiments 1-10 or the method of any one of Embodiments 11-20, wherein the oligonucleotide comprises a nucleic acid sequence having at least 95% sequence identity to SEQ ID NO:44. The kit of any one of Embodiments 1-10 or the method of any one of Embodiments 11-20, wherein the oligonucleotide comprises a nucleic acid sequence having at least 95% sequence identity to SEQ ID NO:45. The kit of any one of Embodiments 1-10 or the method of any one of Embodiments 11-20, wherein the oligonucleotide comprises a nucleic acid sequence having at least 95% sequence identity to SEQ ID NO:46. The kit of any one of Embodiments 1-10 or the method of any one of Embodiments 11-20, wherein the oligonucleotide comprises a nucleic acid sequence having at least 95% sequence identity to SEQ ID NO:47. The kit of any one of Embodiments 1-10 or the method of any one of Embodiments 11-20, wherein the oligonucleotide comprises a nucleic acid sequence having at least 95% sequence identity to SEQ ID NO:48. The kit of any one of Embodiments 1-10 or the method of any one of Embodiments 11-20, wherein the oligonucleotide comprises a nucleic acid sequence having at least 95% sequence identity to SEQ ID NO:49. The kit of any one of Embodiments 1-10 or the method of any one of Embodiments 11-20, wherein the oligonucleotide comprises a nucleic acid sequence having at least 95% sequence identity to SEQ ID NO:50.

Embodiment 25. The kit of any one of Embodiments 1-10 or the method of any one of Embodiments 11-20, wherein the oligonucleotide comprises SEQ ID NO:3. The kit of any one of Embodiments 1-10 or the method of any one of Embodiments 11-20, wherein the oligonucleotide comprises SEQ ID NO:4. The kit of any one of Embodiments 1-10 or the method of any one of Embodiments 11-20, wherein the oligonucleotide comprises SEQ ID NO:5. The kit of any one of Embodiments 1-10 or the method of any one of Embodiments 11-20, wherein the oligonucleotide comprises SEQ ID NO:6. The kit of any one of Embodiments 1-10 or the method of any one of Embodiments 11-20, wherein the oligonucleotide comprises SEQ ID NO:7. The kit of any one of Embodiments 1-10 or the method of any one of Embodiments 11-20, wherein the oligonucleotide comprises SEQ ID NO:8. The kit of any one of Embodiments 1-10 or the method of any one of Embodiments 11-20, wherein the oligonucleotide comprises SEQ ID NO:9. The kit of any one of Embodiments 1-10 or the method of any one of Embodiments 11-20, wherein the oligonucleotide comprises SEQ ID NO:10. The kit of any one of Embodiments 1-10 or the method of any one of Embodiments 11-20, wherein the oligonucleotide comprises SEQ ID NO:11. The kit of any one of Embodiments 1-10 or the method of any one of Embodiments 11-20, wherein the oligonucleotide comprises SEQ ID NO:12. The kit of any one of Embodiments 1-10 or the method of any one of Embodiments 11-20, wherein the oligonucleotide comprises SEQ ID NO:13. The kit of any one of Embodiments 1-10 or the method of any one of Embodiments 11-20, wherein the oligonucleotide comprises SEQ ID NO:14. The kit of any one of Embodiments 1-10 or the method of any one of Embodiments 11-20, wherein the oligonucleotide comprises SEQ ID NO:15. The kit of any one of Embodiments 1-10 or the method of any one of Embodiments 11-20, wherein the oligonucleotide comprises SEQ ID NO:16. The kit of any one of Embodiments 1-10 or the method of any one of Embodiments 11-20, wherein the oligonucleotide comprises SEQ ID NO:17. The kit of any one of Embodiments 1-10 or the method of any one of Embodiments 11-20, wherein the oligonucleotide comprises SEQ ID NO:18. The kit of any one of Embodiments 1-10 or the method of any one of Embodiments 11-20, wherein the oligonucleotide comprises SEQ ID NO:19. The kit of any one of Embodiments 1-10 or the method of any one of Embodiments 11-20, wherein the oligonucleotide comprises SEQ ID NO:20. The kit of any one of Embodiments 1-10 or the method of any one of Embodiments 11-20, wherein the oligonucleotide comprises SEQ ID NO:21. The kit of any one of Embodiments 1-10 or the method of any one of Embodiments 11-20, wherein the oligonucleotide comprises SEQ ID NO:22. The kit of any one of Embodiments 1-10 or the method of any one of Embodiments 11-20, wherein the oligonucleotide comprises SEQ ID NO:23. The kit of any one of Embodiments 1-10 or the method of any one of Embodiments 11-20, wherein the oligonucleotide comprises SEQ ID NO:24. The kit of any one of Embodiments 1-10 or the method of any one of Embodiments 11-20, wherein the oligonucleotide comprises SEQ ID NO:25. The kit of any one of Embodiments 1-10 or the method of any one of Embodiments 11-20, wherein the oligonucleotide comprises SEQ ID NO:26. The kit of any one of Embodiments 1-10 or the method of any one of Embodiments 11-20, wherein the oligonucleotide comprises SEQ ID NO:27. The kit of any one of Embodiments 1-10 or the method of any one of Embodiments 11-20, wherein the oligonucleotide comprises SEQ ID NO:28. The kit of any one of Embodiments 1-10 or the method of any one of Embodiments 11-20, wherein the oligonucleotide comprises SEQ ID NO:29. The kit of any one of Embodiments 1-10 or the method of any one of Embodiments 11-20, wherein the oligonucleotide comprises SEQ ID NO:30. The kit of any one of Embodiments 1-10 or the method of any one of Embodiments 11-20, wherein the oligonucleotide comprises SEQ ID NO:31. The kit of any one of Embodiments 1-10 or the method of any one of Embodiments 11-20, wherein the oligonucleotide comprises SEQ ID NO:32. The kit of any one of Embodiments 1-10 or the method of any one of Embodiments 11-20, wherein the oligonucleotide comprises SEQ ID NO:33. The kit of any one of Embodiments 1-10 or the method of any one of Embodiments 11-20, wherein the oligonucleotide comprises SEQ ID NO:34. The kit of any one of Embodiments 1-10 or the method of any one of Embodiments 11-20, wherein the oligonucleotide comprises SEQ ID NO:35. The kit of any one of Embodiments 1-10 or the method of any one of Embodiments 11-20, wherein the oligonucleotide comprises SEQ ID NO:36. The kit of any one of Embodiments 1-10 or the method of any one of Embodiments 11-20, wherein the oligonucleotide comprises SEQ ID NO:37. The kit of any one of Embodiments 1-10 or the method of any one of Embodiments 11-20, wherein the oligonucleotide comprises SEQ ID NO:38. The kit of any one of Embodiments 1-10 or the method of any one of Embodiments 11-20, wherein the oligonucleotide comprises SEQ ID NO:39. The kit of any one of Embodiments 1-10 or the method of any one of Embodiments 11-20, wherein the oligonucleotide comprises SEQ ID NO:40. The kit of any one of Embodiments 1-10 or the method of any one of Embodiments 11-20, wherein the oligonucleotide comprises SEQ ID NO:41. The kit of any one of Embodiments 1-10 or the method of any one of Embodiments 11-20, wherein the oligonucleotide comprises SEQ ID NO:42. The kit of any one of Embodiments 1-10 or the method of any one of Embodiments 11-20, wherein the oligonucleotide comprises SEQ ID NO:43. The kit of any one of Embodiments 1-10 or the method of any one of Embodiments 11-20, wherein the oligonucleotide comprises SEQ ID NO:44. The kit of any one of Embodiments 1-10 or the method of any one of Embodiments 11-20, wherein the oligonucleotide comprises SEQ ID NO:45. The kit of any one of Embodiments 1-10 or the method of any one of Embodiments 11-20, wherein the oligonucleotide comprises SEQ ID NO:46. The kit of any one of Embodiments 1-10 or the method of any one of Embodiments 11-20, wherein the oligonucleotide comprises SEQ ID NO:47. The kit of any one of Embodiments 1-10 or the method of any one of Embodiments 11-20, wherein the oligonucleotide comprises SEQ ID NO:48. The kit of any one of Embodiments 1-10 or the method of any one of Embodiments 11-20, wherein the oligonucleotide comprises SEQ ID NO:49. The kit of any one of Embodiments 1-10 or the method of any one of Embodiments 11-20, wherein the oligonucleotide comprises SEQ ID NO:50.

Embodiment 26. The kit of any one of Embodiments 1-10 or 21-25 or the method of any one of Embodiments 11-25, wherein the oligonucleotide is a modified oligonucleotide.

Embodiment 27. The kit of any one of Embodiments 1-10 or 21-25 or the method of any one of Embodiments 11-25, wherein the modified oligonucleotide comprises 2'-O-alkyl, 2'O-methyl, 2'-deoxy-2'fluoro, 2'-deoxy, a universal base, 5-C-methyl, an inverted deoxy abasic residue incorporation, a positive backbone, a non-ionic backbone, a modified sugar, a non-ribose backbone, a locked nucleic acid, or a combination of two or more thereof Embodiment 28. The kit of any one Embodiments 1-10 or 21-25 or the method of any one of Embodiments 11-25, wherein the modified oligonucleotide comprises 2'-O-alkyl.

Embodiment 29. The kit of any one Embodiments 1-10 or 21-25 or the method of any one of Embodiments 11-25, wherein the modified oligonucleotide comprises 2'-O-methyl.

Embodiment 30. The kit of any one Embodiments 1-10 or 21-25 or the method of any one of Embodiments 11-25, wherein the modified oligonucleotide comprises 2'-deoxy-2'fluoro.

Embodiment 31. The kit of any one Embodiments 1-10 or 21-25 or the method of any one of Embodiments 11-25, wherein the modified oligonucleotide comprises 2'-deoxy.

Embodiment 32. The kit of any one Embodiments 1-10 or 21-25 or the method of any one of Embodiments 11-25, wherein the modified oligonucleotide comprises a universal base.

Embodiment 33. The kit of any one Embodiments 1-10 or 21-25 or the method of any one of Embodiments 11-25, wherein the modified oligonucleotide comprises 5-C-methyl.

Embodiment 34. The kit of any one Embodiments 1-10 or 21-25 or the method of any one of Embodiments 11-25, wherein the modified oligonucleotide comprises an inverted deoxy abasic residue incorporation.

Embodiment 35. The kit of any one Embodiments 1-10 or 21-25 or the method of any one of Embodiments 11-25, wherein the modified oligonucleotide comprises a positive backbone.

Embodiment 36. The kit of any one Embodiments 1-10 or 21-25 or the method of any one of Embodiments 11-25, wherein the modified oligonucleotide comprises a non-ionic backbone.

Embodiment 37. The kit of any one Embodiments 1-10 or 21-25 or the method of any one of Embodiments 11-25, wherein the modified oligonucleotide comprises a modified sugar.

Embodiment 38. The kit of any one Embodiments 1-10 or 21-25 or the method of any one of Embodiments 11-25, wherein the modified oligonucleotide comprises a non-ribose backbone.

Embodiment 39. The kit of any one Embodiments 1-10 or 21-25 or the method of any one of Embodiments 11-25, wherein the modified oligonucleotide comprises a locked nucleic acid.

Embodiment 40. The kit of any one Embodiments 1-10 or 21-25 or the method of any one of Embodiments 11-25, wherein the modified oligonucleotide comprises a morpholino modification.

Embodiment 40. The kit of any one Embodiments 1-10 or 21-25 or the method of any one of Embodiments 11-25, wherein the modified oligonucleotide comprises a morpholino modification and a 2'-O-methyl.

Embodiment 41. An isolated nucleic acid sequence comprising SEQ ID NO:3. An isolated nucleic acid sequence comprising SEQ ID NO:4. An isolated nucleic acid sequence comprising SEQ ID NO:5. An isolated nucleic acid sequence comprising SEQ ID NO:6. An isolated nucleic acid sequence comprising SEQ ID NO:7. An isolated nucleic acid sequence comprising SEQ ID NO:8. An isolated nucleic acid sequence comprising SEQ ID NO:9. An isolated nucleic acid sequence comprising SEQ ID NO:10. An isolated nucleic acid sequence comprising SEQ ID NO:11. An isolated nucleic acid sequence comprising SEQ ID NO:12. An isolated nucleic acid sequence comprising SEQ ID NO:13. An isolated nucleic acid sequence comprising SEQ ID NO:14. An isolated nucleic acid sequence comprising SEQ ID NO:15. An isolated nucleic acid sequence comprising SEQ ID NO:16. An isolated nucleic acid sequence comprising SEQ ID NO:17. An isolated nucleic acid sequence comprising SEQ ID NO:18. An isolated nucleic acid sequence comprising SEQ ID NO:19. An isolated nucleic acid sequence comprising SEQ ID NO:20. An isolated nucleic acid sequence comprising SEQ ID NO:21. An isolated nucleic acid sequence comprising SEQ ID NO:22. An isolated nucleic acid sequence comprising SEQ ID NO:23. An isolated nucleic acid sequence comprising SEQ ID NO:24. An isolated nucleic acid sequence comprising SEQ ID NO:25. An isolated nucleic acid sequence comprising SEQ ID NO:26. An isolated nucleic acid sequence comprising SEQ ID NO:27. An isolated nucleic acid sequence comprising SEQ ID NO:28. An isolated nucleic acid sequence comprising SEQ ID NO:29. An isolated nucleic acid sequence comprising SEQ ID NO:30. An isolated nucleic acid sequence comprising SEQ ID NO:31. An isolated nucleic acid sequence comprising SEQ ID NO:32. An isolated nucleic acid sequence comprising SEQ ID NO:33. An isolated nucleic acid sequence comprising SEQ ID NO:34. An isolated nucleic acid sequence comprising SEQ ID NO:35. An isolated nucleic acid sequence comprising SEQ ID NO:36. An isolated nucleic acid sequence comprising SEQ ID NO:37. An isolated nucleic acid sequence comprising SEQ ID NO:38. An isolated nucleic acid sequence comprising SEQ ID NO:39. An isolated nucleic acid sequence comprising SEQ ID NO:40. An isolated nucleic acid sequence comprising SEQ ID NO:41. An isolated nucleic acid sequence comprising SEQ ID NO:42. An isolated nucleic acid sequence comprising SEQ ID NO:43. An isolated nucleic acid sequence comprising SEQ ID NO:44. An isolated nucleic acid sequence comprising SEQ ID NO:45. An isolated nucleic acid sequence comprising SEQ ID NO:46. An isolated nucleic acid sequence comprising SEQ ID NO:47. An isolated nucleic acid sequence comprising SEQ ID NO:48. An isolated nucleic acid sequence comprising SEQ ID NO:49. An isolated nucleic acid sequence comprising SEQ ID NO:50.

Embodiment 42. The isolated nucleic acid sequence of Embodiment 41, which comprises a modification to at least one nucleotide.

Embodiment 43. The isolated nucleic acid of Embodiment 42, wherein the modification is 2'-O-alkyl, 2' O-methyl, 2'-deoxy-2'fluoro, 2'-deoxy, a universal base, 5-C-methyl, an inverted deoxy abasic residue incorporation, a positive backbone, a non-ionic backbone, a modified sugar, a non-ribose backbone, a locked nucleic acid, or a combination of two or more thereof.

Embodiment 44. The isolated nucleic acid of Embodiment 42, wherein the modification is a morpholino modification.

Embodimnet 45. The isolated nucleic acid of Embodiment 42, wherein the modified oligonucleotide comprises a 2'-O-methyl modification.

Embodiment 46. The isolated nucleic acid of Embodiment 42, wherein the modified oligonucleotide comprises a 2'-O-methyl modification and a morpholino modification.

Embodiment 47. An isolated nucleic acid sequence comprising SEQ ID NO:1.

Embodiment 48. An isolated nucleic acid sequence comprising SEQ ID NO:2.

EXAMPLE

A number of clinical trials use lentiviral constructs containing shRNAs inside of miNRA intronic cassettes. Unfortunately, these vectors have varying levels of self-repression during lentiviral packaging due to vector targeting by processed shRNAs and as a result, viral titer remains low in large-scale productions. One potential target for increasing viral production is splicing since it is an early modulator of intronic shRNA processing. It has previously been shown that the MCM7 miRNA 106b-25 cluster uses alternative splicing to control expression of its three miRNAs and that inhibition of these sites can drive expression of the miRNAs to varying levels. It was also found that splice-inhibiting antisense oligonucleotides can modulate gene expression and RISC-complex loading of shRNAs. Therefore, using splice-inhibiting antisense oligonucleotides during packaging should allow intact viral production and improved overall titer.

Hematopoietic malignancies are characterized by an inability of the immune system to function correctly and if left untreated, are fatal. Treatments to date include bone marrow transplants and in some cases like Human Immunodeficiency Virus (HIV)-lymphoma patients, techniques such as lentiviral transduction, electroporation, or zinc-finger nucleases have been used to genetically-modify transplant cells in order to also protect these patients from HIV infection. One pre-clinical therapy uses a lentivirus that incorporates a minichromosome maintenance complex component 7 (MCM7) gene cassette that contains artificial short-hairpin ribonucleic acids (shRNAs) in its intron that target different HIV genes.

MCM7 is a regulatory gene responsible for various replication events including pre-replication complex and replication fork formation and it contains three endogenous microRNAs (miRNAs) that assist in these processes. When knocked down or alternatively spliced, the MCM7 miRNAs are overexpressed and are indications of many cancers including breast, colon, and pancreatic cancers. These intronic miRNAs have also been shown to rely on spliceosomal activity for efficient miRNA biogenesis and their expression levels can be modulated using splice-inhibiting morpholinos.

Packaging efficiency of shRNA-containing vectors and especially the MCM7 cassette vectors is a known hurdle in clinical lentiviral production. In an attempt to improve viral titer, various anti-sense oligonucleotides (ASOs) can be used to target splice junctions and alternative splice sites of the lentiviral MCM7 gene cassette. These ASOs bind selectively to RNA and can affect splicing events. To test this, third generation MCM7 vectors have been packaged in the presence or absence of splice-inhibiting ASOs into HEK 293T cells to make lentivirus. Viral titer has been determined and the transduced cells will be tested for alternative splicing of the MCM7 cassette. ASO-treated viral titer increased for both initial tests and small-scale viral production. These results indicate that clinical lentiviral production of MCM7 vectors would benefit from the incorporation of splice-inhibiting ASOs during packaging.

Materials and Methods. Antisense oligonucleotide production. Morpholinos and 2'-OMe-modified oligonucleotides were prepared. Lentiviral packaging with splice-inhibiting ASOs. Lentiviral plasmid was co-transfected with gag/pol, rev, and VSVG packaging plasmids into 100 mm plates with 60-75% confluent 293T cells. Viral supernatant was harvested 48 hours later (preliminary test) or pooled from 24, 48, and 72 hours (small-scale test). Lentiviral transduction and titering. 293T or HT1080 cells were grown in DMEM supplemented with 10% FBS and L-Glutamine. Cells were plated into 12-well plates for 50% confluency on transduction day. Varying volumes of filtered raw viral supernatant were added to each well along with polybrene (0.8 ug/mL final). Viral supernatant was removed 12 hours later and replaced with fresh media. Cells were allowed to grow for 5 days and passaged when confluent. On Day 5, cells were harvested and divided into two groups. One group was resuspended in Trizol for later RNA and DNA extraction, while the second group was stained with DAPI and analyzed by flow cytometry for GFP expression in live cell populations. Statistical Analysis. GFP and MOI calculations were calculated using Poisson distribution.

Conclusions. Splice-inhibiting antisense oligonucleotides can be used to increase viral production of miRNA cassette lentiviruses. Virus produced by these packaging experiments can efficiently transduce 293T and HT1080 cells. Some ASOs appear to be more effective at increasing viral titer than others. ASOs that suppress viral production may be interfering with packaging processes and remain to be investigated further.

Future Directions. Further ASO construct development and testing. Explore other delivery methods. Cell-type validation assays. Large-scale packaging (clinical scale). Comparative studies with other lentiviral titer improvement strategies and viral constructs. If all goes well, incorporation into current clinical manufacturing processes.

Significance. shRNA-mediated gene therapy continues to be a major player in functional disease treatments for heme malignancies and potentially more diseases. Large-scale production of lentiviruses that contain miRNA cassettes have historically had lower titers than normal shRNA-containing vectors and increase of viral titer would decrease cost and materials used for clinical viral production.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Liu et al (2011) Biochimica et biophysica acta. 1809: 732-45; McCarron et al (2016) *Journal of biotechnology.* 240: 23-30; Merten et al (2011) *Human gene therapy.* 22: 343-56; Liu et al (2010) *RNA* (New York, N.Y.). 16: 1328-39; Aagaard et al, (2008) *Gene therapy.* 15: 1536-49; Chung et al (2012) Human gene therapy. 23: 1200-8; Liu et al (2011) *Biochimica et biophysica acta.* 1809: 732-45; Agranat-Tamir et al (2014) *Nucleic acids research.* 42: 4640-51. PMID: 24464992; PMCID: PMC3985634

What is claimed is:

1. A kit comprising an oligonucleotide which comprises a mirtron splice site binding sequence; and a lentiviral packaging system;
   wherein the oligonucleotide comprises a nucleic acid sequence selected from the group consisting of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; and SEQ ID NO:26; and
   wherein the oligonucleotide comprises a modification to at least one nucleotide, and wherein the modification is a morpholino modification, a 2'-O-methyl modification, or a combination thereof.

2. The kit of claim 1, wherein the lentiviral packaging system is a second generation lentiviral packaging system or a third generation lentiviral packaging system.

3. The kit of claim 1, wherein the oligonucleotide comprises the nucleic acid sequence of SEQ ID NO:7.

4. The kit of claim 1, wherein the oligonucleotide further comprises a modification of 2'-O-alkyl, 2'-deoxy-2'fluoro, 2'-deoxy, a universal base, 5-C-methyl, an inverted deoxy abasic residue incorporation, a positive backbone, a non-ionic backbone, a modified sugar, a non-ribose backbone, a locked nucleic acid, or a combination of two or more thereof, to at least one nucleotide.

5. The kit of claim 1, wherein the modification is the morpholino modification or the 2'-O-methyl modification.

6. The kit of claim 1, wherein the mirtron splice site binding sequence comprises: (i) a nucleic acid that binds to a region of the MCM7 splice donor site, or (ii) a nucleic acid that binds to a region of the MCM7 splice acceptor site.

7. The kit of claim 1, further comprising a bacterial cell, a eukaryotic cell, a T cell, a HT1080 cell, or a HEK293T cell.

8. A method for producing a lentivirus, the method comprising the step of: transfecting a cell with an oligonucleotide comprising a mirtron splice site binding sequence, and a lentiviral packaging system; thereby producing the lentivirus;
   wherein the oligonucleotide comprises a nucleic acid sequence selected from the group consisting of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; and SEQ ID NO:26; and
   wherein the oligonucleotide comprises a modification to at least one nucleotide, and wherein the modification is a morpholino modification, a 2'-O-methyl modification, or a combination thereof.

9. The method of claim 8, wherein the cell is a bacterial cell, a eukaryotic cell, a T cell, a HT1080 cell, or a HEK293T cell.

10. The method of claim 8, wherein the lentivirus is a pHIV7-EGFP lentivirus.

11. The method of claim 8, wherein the mirtron splice site binding sequence comprises: (i) a nucleic acid that binds to a region of the MCM7 splice donor site, or (ii) a nucleic acid that binds to a region of the MCM7 splice acceptor site.

12. The method of claim 8, wherein the oligonucleotide comprises the nucleic acid sequence of SEQ ID NO:7.

13. The method of claim 8, wherein the oligonucleotide further comprises a modification selected from the group consisting of 2'-O-alkyl, 2'-deoxy-2'fluoro, 2'-deoxy, a universal base, 5-C-methyl, an inverted deoxy abasic residue incorporation, a positive backbone, a non-ionic backbone, a modified sugar, a non-ribose backbone, a locked nucleic acid, or a combination of two or more thereof, to at least one nucleotide.

14. The method of claim 8, wherein the modification is the morpholino modification or the 2'-O-methyl modification.

15. An isolated nucleic acid sequence comprising SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22, SEQ ID NO:23; SEQ ID NO:24; SEQ ID NO:25; or SEQ ID NO:26;
   wherein the isolated nucleic acid sequence comprises a modification to at least one nucleotide, and wherein the modification is a morpholino modification, a 2'-O-methyl modification, or a combination thereof.

16. The isolated nucleic acid sequence of claim 15, which comprises SEQ ID NO:7.

17. The isolated nucleic acid of claim 15, wherein the isolated nucleic acid sequence further comprises a modification selected from the group consisting of is 2'-O-alkyl, 2'-deoxy-2'fluoro, 2'-deoxy, a universal base, 5-C-methyl, an inverted deoxy abasic residue incorporation, a positive backbone, a non-ionic backbone, a modified sugar, a non-ribose backbone, a locked nucleic acid, or a combination of two or more thereof, to at least one nucleotide.

18. The isolated nucleic acid of claim 15, wherein the modification is the morpholino modification or the 2'-O-methyl modification.

* * * * *

```
                           SEQUENCE LISTING

<160> NUMBER OF SEQ ID NOS: 50

<210> SEQ ID NO 1
<211> LENGTH: 50
<212> TYPE: RNA
<213> ORGANISM: Artificial sequence
<220> FEATURE:
<223> OTHER INFORMATION: Synthetic polynucleotide

<400> SEQUENCE: 1
ucuuuccccc cuaccuuccc cuuaggcacg ucugagaaug guggaugugg              50

<210> SEQ ID NO 2
<211> LENGTH: 50
<212> TYPE: RNA
<213> ORGANISM: Artificial sequence
<220> FEATURE:
<223> OTHER INFORMATION: Synthetic polynucleotide

<400> SEQUENCE: 2
uauccugcgc cuuuccacug cucugguaag ugcccaaauu gcuggagggc              50

<210> SEQ ID NO 3
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 3
ccctccagca atttgggcac ttacc                                        25

<210> SEQ ID NO 4
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 4
cctccagcaa tttgggcact tacca                                        25

<210> SEQ ID NO 5
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 5
ctccagcaat ttgggcactt accag                                        25
```

```
<210> SEQ ID NO 6
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 6
tccagcaatt tgggcactta ccaga                                25

<210> SEQ ID NO 7
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 7
ccagcaattt gggcacttac cagag                                25

<210> SEQ ID NO 8
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 8
cagcaatttg ggcacttacc agagc                                25

<210> SEQ ID NO 9
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 9
agcaatttgg gcacttacca gagca                                25

<210> SEQ ID NO 10
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 10
gcaatttggg cacttaccag agcag                                25

<210> SEQ ID NO 11
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 11
caatttgggc acttaccaga gcagt                                25

<210> SEQ ID NO 12
<211> LENGTH: 25
<212> TYPE: DNA
<213> ORGANISM: Artificial sequence
<220> FEATURE:
```

<223> OTHER INFORMATION: Synthetic polynucleotide

<400> SEQUENCE: 12
aatttgggca cttaccagag cagtg                                25

<210> SEQ ID NO 13
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 13
atttgggcac ttaccagagc agtgg                                25

<210> SEQ ID NO 14
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 14
tttgggcact taccagagca gtgga                                25

<210> SEQ ID NO 15
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 15
ttgggcactt accagagcag tggaa                                25

<210> SEQ ID NO 16
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 16
tgggcactta ccagagcagt ggaaa                                25

<210> SEQ ID NO 17
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 17
gggcacttac cagagcagtg gaaag                                25

<210> SEQ ID NO 18
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 18
ggcacttacc agagcagtgg aaagg                                25

```
<210> SEQ ID NO 19
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 19
gcacttacca gagcagtgga aaggc                                              25

<210> SEQ ID NO 20
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 20
cacttaccag agcagtggaa aggcg                                              25

<210> SEQ ID NO 21
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 21
acttaccaga gcagtggaaa ggcgc                                              25

<210> SEQ ID NO 22
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 22
cttaccagag cagtggaaag gcgca                                              25

<210> SEQ ID NO 23
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 23
ttaccagagc agtggaaagg cgcag                                              25

<210> SEQ ID NO 24
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 24
taccagagca gtggaaaggc gcagg                                              25

<210> SEQ ID NO 25
<211> LENGTH: 25
<212> TYPE: DNA
<213> ORGANISM: Artificial sequence
<220> FEATURE:
<223> OTHER INFORMATION: Synthetic polynucleotide
```

<400> SEQUENCE: 25
accagagcag tggaaaggcg cagga    25

<210> SEQ ID NO 26
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 26
ccagagcagt ggaaaggcgc aggat    25

<210> SEQ ID NO 27
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 27
cacatccacc attctcagac gtgcc    25

<210> SEQ ID NO 28
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 28
acatccacca ttctcagacg tgcct    25

<210> SEQ ID NO 29
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 29
catccaccat tctcagacgt gccta    25

<210> SEQ ID NO 30
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 30
atccaccatt ctcagacgtg cctaa    25

<210> SEQ ID NO 31
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 31
tccaccattc tcagacgtgc ctaag    25

<210> SEQ ID NO 32
<211> LENGTH: 25

```
<212> TYPE: DNA
<213> ORGANISM: Artificial sequence
<220> FEATURE:
<223> OTHER INFORMATION: Synthetic polynucleotide

<400> SEQUENCE: 32
ccaccattct cagacgtgcc taagg                                         25

<210> SEQ ID NO 33
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 33
caccattctc agacgtgcct aaggg                                         25

<210> SEQ ID NO 34
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 34
accattctca gacgtgccta agggg                                         25

<210> SEQ ID NO 35
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 35
ccattctcag acgtgcctaa gggga                                         25

<210> SEQ ID NO 36
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 36
cattctcaga cgtgcctaag gggaa                                         25

<210> SEQ ID NO 37
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 37
attctcagac gtgcctaagg ggaag                                         25

<210> SEQ ID NO 38
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 38
```
ttctcagacg tgcctaaggg gaagg                                              25

<210> SEQ ID NO 39
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 39
tctcagacgt gcctaagggg aaggt                                              25

<210> SEQ ID NO 40
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 40
ctcagacgtg cctaagggga aggta                                              25

<210> SEQ ID NO 41
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 41
tcagacgtgc ctaagggaa ggtag                                               25

<210> SEQ ID NO 42
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 42
cagacgtgcc taaggggaag gtagg                                              25

<210> SEQ ID NO 43
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 43
agacgtgcct aaggggaagg taggg                                              25

<210> SEQ ID NO 44
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 44
gacgtgccta aggggaaggt agggg                                              25

<210> SEQ ID NO 45
<211> LENGTH: 25
<212> TYPE: DNA
<213> ORGANISM: Artificial sequence

```
<220> FEATURE:
<223> OTHER INFORMATION: Synthetic polynucleotide

<400> SEQUENCE: 45
acgtgcctaa ggggaaggta ggggg                                              25

<210> SEQ ID NO 46
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 46
cgtgcctaag gggaaggtag ggggg                                              25

<210> SEQ ID NO 47
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 47
gtgcctaagg ggaaggtagg gggga                                              25

<210> SEQ ID NO 48
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 48
tgcctaaggg gaaggtaggg gggaa                                              25

<210> SEQ ID NO 49
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 49
gcctaagggg aaggtagggg ggaaa                                              25

<210> SEQ ID NO 50
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 50
cctaagggga aggtaggggg gaaag                                              25
```